United States Patent [19]
Ellinwood, Jr.

[11] 4,146,029
[45] * Mar. 27, 1979

[54] SELF-POWERED IMPLANTED PROGRAMMABLE MEDICATION SYSTEM AND METHOD

[76] Inventor: Everett H. Ellinwood, Jr., 3519 Tonbridge Way, Durham, N.C. 27707

[*] Notice: The portion of the term of this patent subsequent to Dec. 2, 1992, has been disclaimed.

[21] Appl. No.: 802,118

[22] Filed: May 31, 1977

Related U.S. Application Data

[63] Continuation of Ser. No. 636,219, Nov. 28, 1975, abandoned, which is a continuation-in-part of Ser. No. 463,262, Apr. 23, 1974, Pat. No. 3,923,060.

[51] Int. Cl.² .............................................. A61M 5/20
[52] U.S. Cl. ............................... 128/260; 128/206 A; 128/419 P
[58] Field of Search ..................... 128/1 R, 20, 2.0 B, 128/2.0 A, 2.0 R, 2.1 E, 173, 213, 214 E, 214 F, 260, 419 E, 419 P, 419 PG, 419 PS, 422, 423, DIG. 12, DIG. 13; 3/1.7

[56] References Cited

U.S. PATENT DOCUMENTS

| | | | |
|---|---|---|---|
| 3,527,220 | 9/1970 | Summers | 128/260 |
| 3,662,758 | 5/1972 | Glover | 128/419 G |
| 3,680,544 | 8/1972 | Shinnick et al. | 128/418 |
| 3,692,027 | 9/1972 | Ellinwood, Jr. | 128/260 |
| 3,727,616 | 4/1973 | Lenzkgs | 128/422 |
| 3,837,339 | 9/1974 | Aisenberg et al. | 128/213 |
| 3,871,361 | 3/1975 | Kamen | 128/213 |
| 3,871,382 | 3/1975 | Mann | 128/419 P |
| 3,894,538 | 7/1975 | Richter | 128/260 |
| 4,034,757 | 7/1977 | Glover | 128/260 |
| 4,055,175 | 10/1977 | Clemens | 128/260 |

Primary Examiner—William E. Kamm
Attorney, Agent, or Firm—B. B. Olive

[57] ABSTRACT

A device and method for dispensing medication internally of the body utilize an implanted system which includes medication storage and dispensing control circuitry having control components which may be modified by means external of the body being treated to control the manner of dispensing the medication within such body. Coordinated pacemaking is also available.

27 Claims, 30 Drawing Figures

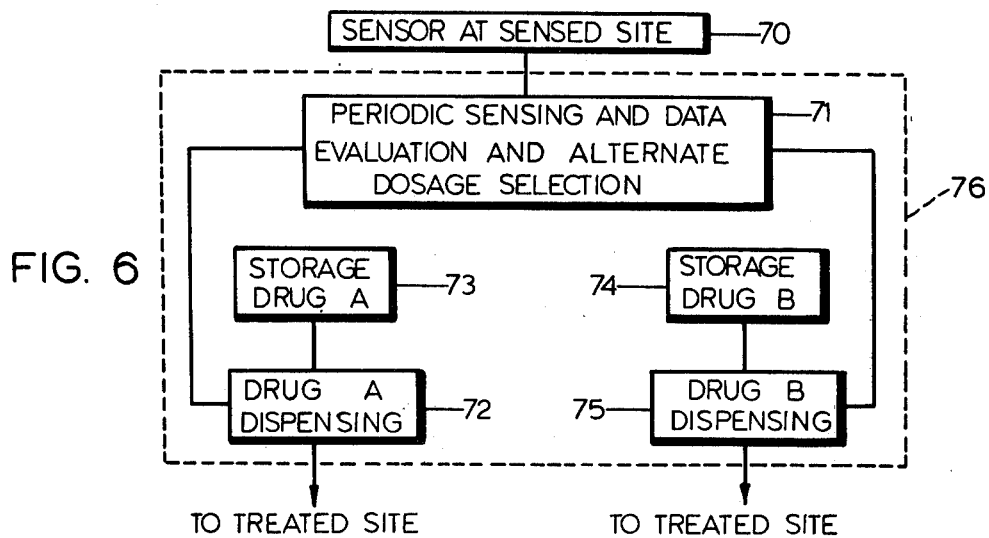
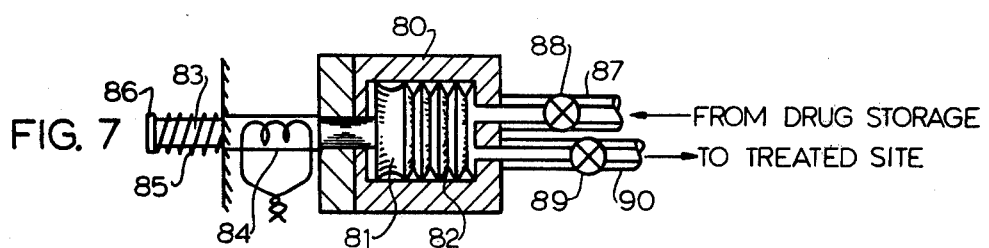
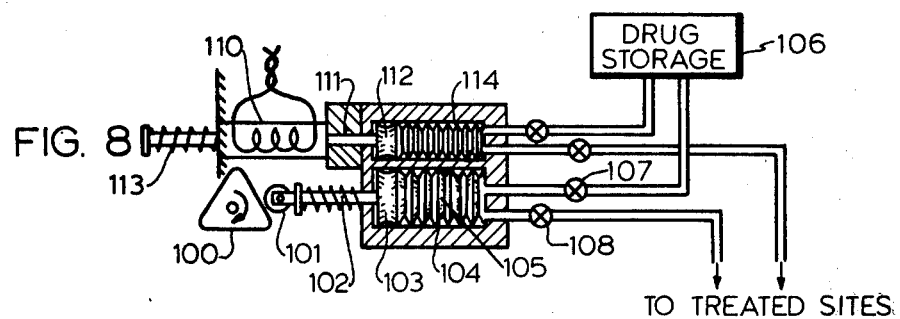
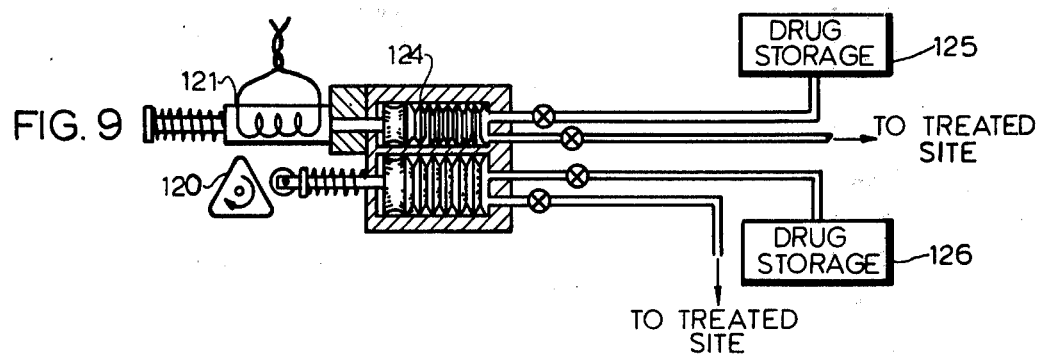

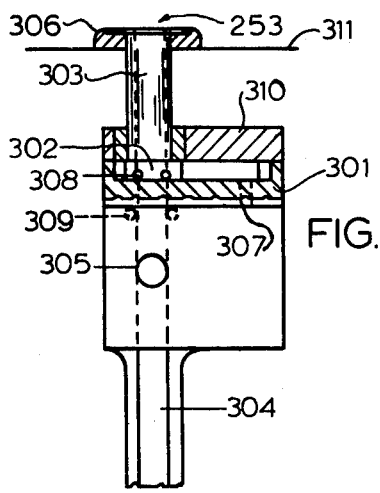
FIG. 14
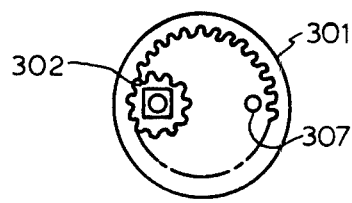
FIG. 14 A
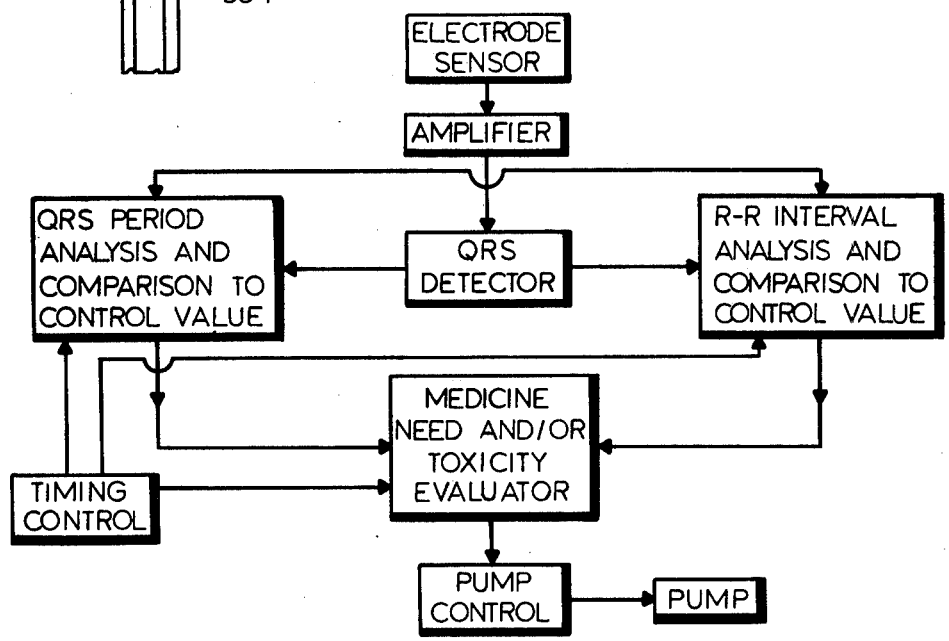
FIG. 15
FIG. 17
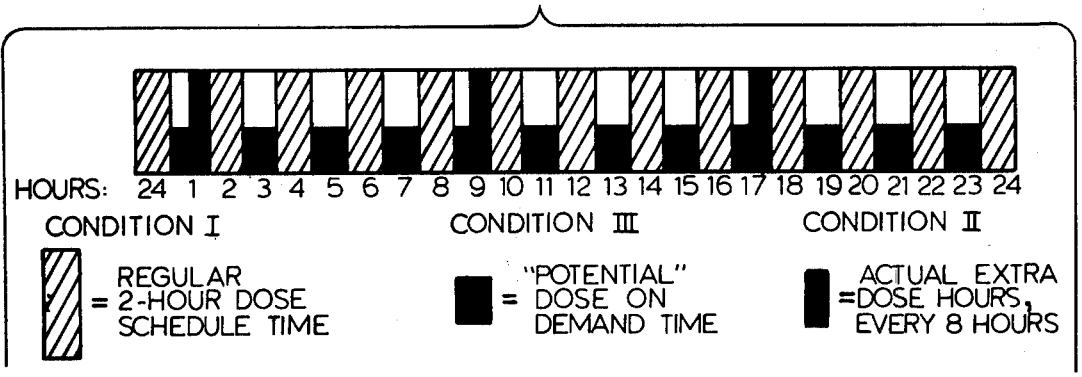

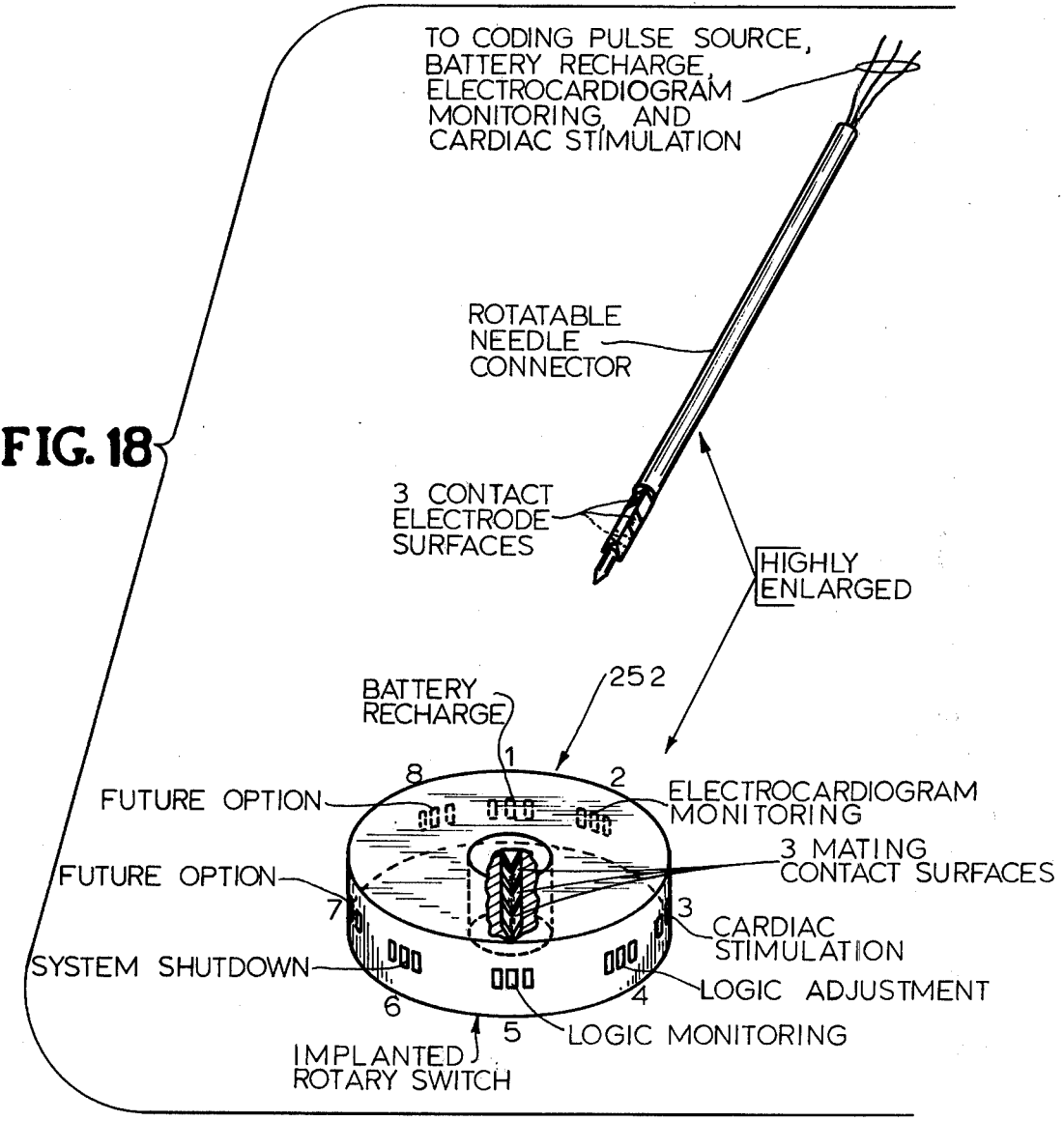

SELF-POWERED IMPLANTED PROGRAMMABLE MEDICATION SYSTEM AND METHOD

CROSS-REFERENCE TO RELATED APPLICATIONS

This is a continuation of application Ser. No. 636,219, filed Nov. 28, 1975, and now abandoned, which in turn is a continuation-in-part of application Ser. No. 463,262, filed Apr. 23, 1974, now U.S. Pat. No. 3,923,060.

BACKGROUND OF THE INVENTION

1. Field of the Invention

The invention relates to implanted apparatus for dispensing medical or physiological substances. More specifically, the invention relates to a device and method principally concerned with using the control circuitry in an implanted medication system to provide medication programs responsive to the needs of the patient at particular times.

2. Description of the Prior Art

A review of prior art practices with regard to dispensing medical substances internally of the body has previously been given in my prior U.S. Pat. No. 3,692,027 to which reference is made. Also, a summary of such related prior art practices is given in my copending application, Ser. No. 463,262, now U.S. Pat. No. 3,923,060, to which reference is also made. The general background of the prior art is believed to have been also described or cited in my U.S. Pat. No. 3,923,060 and otherwise adequately explained in my prior patent and copending application and, therefore, will not be repeated here.

The present invention is primarily directed to devices and methods for dispensing substances internally of the body and which in some way utilize implanted components whose operational modes can be controlled externally of the body. So far as I am aware, my prior U.S. Pat. No. 3,692,027 provides the first teaching of a self-powered device which can be implanted and which is adapted to dispense medical substances in premeasured doses at specific intervals over a long period of time. The device and method of my prior U.S. Pat. No. 3,692,027 has been improved upon by the subject matter of my copending application, now U.S. Pat. No. 3,923,060, by providing means for sensing internal body conditions and for evaluating the sensed data in order to control both the conditions under which and the kind of dispensing which takes place.

In U.S. Pat. No. 3,923,060 there is described for one embodiment a logic flow chart for an implanted discrete electronic component medication dispensing system and an externally accessible switch which enables the implanted control circuit configuration to be changed by a needle-switch operator located externally of the body. Thus, there is provided a means for changing the implanted circuit configuration to vary the control system which controls the manner in which the stored substances are dispensed. Much of the referred to description of the copending application is later repeated in the specification of this application and is noted here primarily for the purpose of pointing out that the present invention is concerned with both the needle operator-rotary switch technique for extracorporeal circuit control as well as with a dramatically improved means and method for circuit modification of implanted dispensing control circuitry to provide a treatment more compatible with actual need.

The emphasis of the present invention is thus directed to providing implanted control circuitry for controlling the dispensing of medication and which circuitry can be modified by means located external of the body. In this regard, it may be noted that U.S. Pat. No. 3,527,220 has previously taught the practice of implanting a medication storage container, a pump connected to pump the medication from the container to a site within the body, and means by which the pump can be powered through an extracorporeal magnetic field. This patent reference also teaches the practice of having an implanted switch whose action can be controlled by an extracorporeal magnetic field. The system taught by U.S. Pat. No. 3,527,220, however, basically has only an on-off capability and no programming capability. That is, there is no choice of circuit configurations which can be modified by an extracorporeal control to provide a variety of programs for dispensing the medication. The system of U.S. Pat. No. 3,527,220 also noticeably lacks any means for sensing internal body conditions and using the sensed data as a means for controlling the dispensing of medication.

With respect to extracorporeal control of implanted programmable circuitry, U.S. Pat. No. 3,833,005 illustrates a cardiac "pacemaker" type device which uses an extracorporeal transmitter to provide control signals to the pacemaker receiver and from there to the control circuitry. The control circuitry includes memory, counting and logic circuitry which provides a simple programming capability for rate and amplitude control for pacemaking purposes but has no medication dispensing mechanism.

The prior art practices concerned with implanting artificial and replacement material organs should also be noted. Of particular interest to the present invention is the recent development in Canada of a non-implanted but computerized artificial pancreas in which blood sugar is monitored and insulin or dextrose is delivered according to need. This development is also reported in a Post Times Service news release of Apr. 18, 1974 and is described in the Medical Tribune and Medical News issue of Oct. 9, 1974, and the articles suggest the possibility of developing a miniaturized, implantable artificial pancreas.

Another prior art development related to the present invention concerns the availability of what are called microprocessors. In this regard, reference may be made to an article appearing in the Apr. 18, 1974 issue of Electronics Magazine. As explained in this article, the availability of a microprocessor drastically reduces the cost and also the size of the circuitry required to provide programming capability in miniaturized circuits. By adding appropriate memory devices to the microprocessor and applicable input and output circuits, there becomes available a micro-miniaturized programmable circuit with a versatile programming characteristic, highly adaptable input/output system capabilities, minimum parts count and easy expansion through modular architecture. The current Fairchild F-8 microprocessor series provides such a system. From the foregoing, it can be seen that while the implanted system and method for dispensing medical substances, as taught in U.S. Pat. No. 3,923,060, provides a unique system and a method for a limited programmable system for periodically evaluating selected states of the body and dispensing medical substances accordingly while leaving the patient ambulatory, the present invention recognizes that further improvements could be made by embodying a micro-miniaturized more adaptable programming capability and a system and method which would lend itself to extracorporeal control of such capability and to reprogramming.

SUMMARY OF THE INVENTION

The apparatus and method of the invention is based on storage, control and dispensing components of a unitary device being entirely implanted in the body but with selected control components being adapted to extracorporeal operator control. There is provided either one or a plurality of sensors, each of which is adapted to sense a particular body condition at a particular point in the body. There is also provided a self-powered medication dispensing apparatus whose operation is made dependent on evaluation of changes in the sensed data. The dispensing apparatus and method of the invention can be directed to one or a plurality of medical substances in powdered, liquid, suspension, or other dispensable form. The decision making capability of the invention, which functions on a basis of changes in the sensed data, controls when the dispensing apparatus operates and therefore controls the dispensing of medication according to the specific needs of the patient at specific times.

Of particular importance to the present invention is the capability of having the internal implanted circuitry modified by extracorporeal control means so as to provide a selectable, programming capability. Thus, for example, a variety of timing programs can be selected by extracorporeal control. Similarly, a variety of data evaluation programs or dispensing options can be selected by extracorporeal control with the employment of microprocessor techniques and similar micro-miniaturization circuit techniques. The choice of such circuit programs becomes essentially infinite. In one embodiment, extracorporeal control and internal circuit changes are obtained by an operatively associated externally inserted needle operator and needle-operated rotary switch. In another embodiment, the extracorporeal control is provided by a pulse transmitter adapted to provide coded pulses which can be interpreted by the implanted circuitry to achieve selected medication programs corresponding to particular codes.

As compared to the prior specification of copending application Ser. No. 463,262, the present specification repeats and supplements the prior specification by illustrating a system and method based on either direct replacement of the digital circuitry of the prior application or on replacement of the entire circuitry of the prior application with a microprocessor system having an appropriate interface for extracorporeal communication. Thus, the present invention provides a much improved method for an implanted medication system both because of the reprogrammable character as well as by reason of an improved interface through which extracorporeal communication with the implanted system may be obtained. More specifically, the interface portion of the circuitry of the present invention lends itself to use of a variety of peripheral devices such as memory latch controls, various types of remotely operable switches, R-F transmitters and receivers through which information may be sent to and from the implanted microprocessor circuitry in the form of programming changes, operation constraints, and the like. Information processed by the microprocessor system can also be transmitted to suitable peripheral devices of the kind indicated. As with the method and system described in the specification of U.S. Pat. No. 3,923,060, the system of the present invention which incorporates the improved micro-miniaturized microprocessor circuitry lends itself to being housed in a unitary housing having appropriate compartments for the medication storage, the micro-power source, the micro-miniaturized programmable control circuitry and the controlled dispensing means.

DESCRIPTIONS OF THE DRAWINGS

In respect to the following figure descriptions, it should be noted that FIGS. 1-17 and the descriptions thereof are used in both the present application and in U.S. Pat. No. 3,923,060, since such drawings apply to and help explain the separate subject matter being claimed in the present application as well as in U.S. Pat. No. 3,923,060.

FIG. 6 is a block diagram illustrating application of the invention to dispensing different medications to different sites.

FIG. 7 is a somewhat schematic and enlarged diagram of a miniature bellows pumping device useful in the invention.

FIG. 8 is a somewhat schematic enlarged view of a multiple bellows-type pump for dispensing the same medication to the same site but in different quantities and under different conditions.

FIG. 9 is a somewhat schematic enlarged diagram of a multiple bellows-type pump for dispensing separate kinds of medication to separate sites in different quantities and under separate controls.

FIGS. 14 and 14A schematically illustrate a portal arrangement for replenishing medication to the system.

FIG. 15 is a block diagram of the decision-making circuitry.

Figure 16:
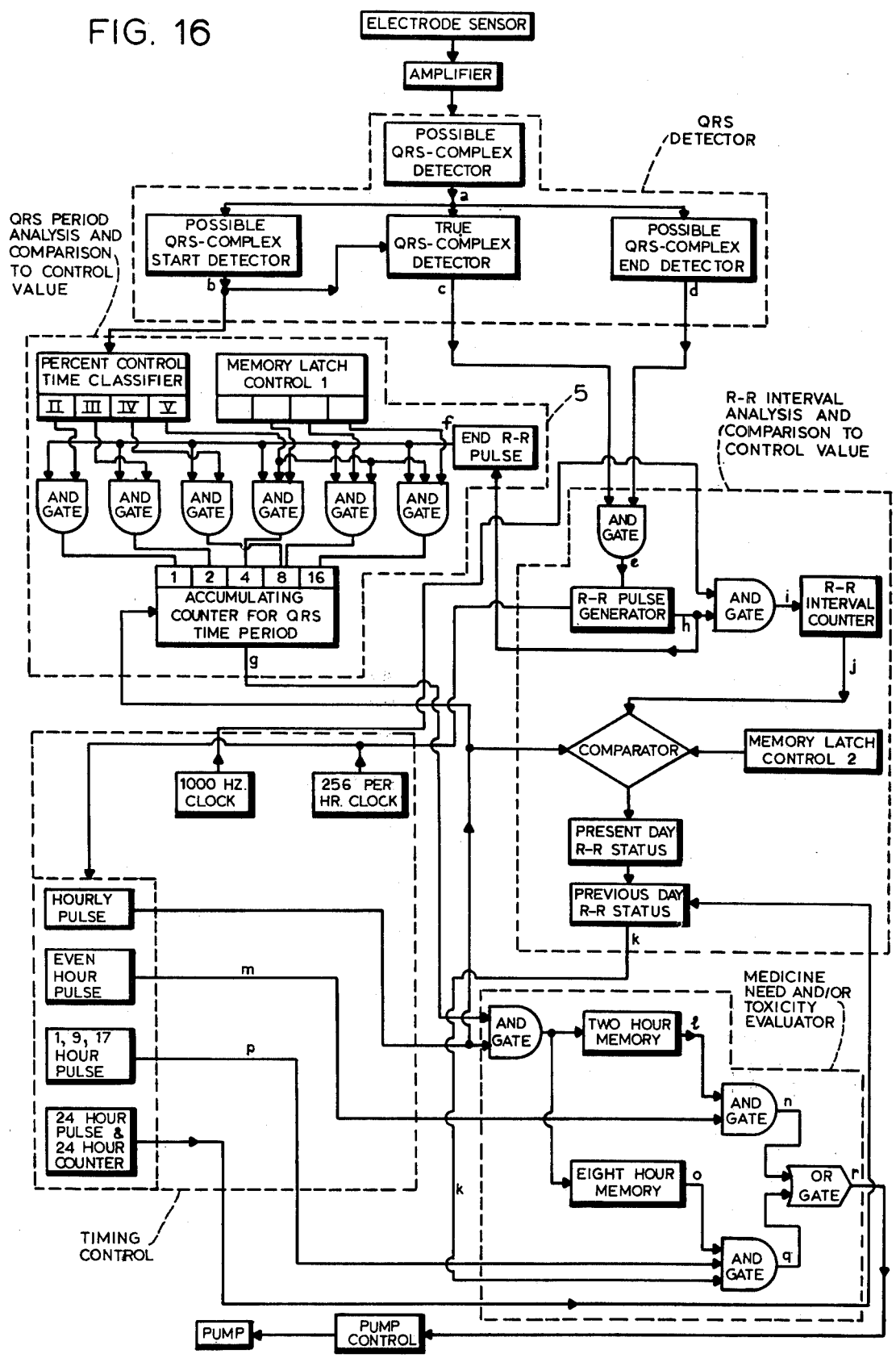

FIG. 16 is a more detailed circuit diagram corresponding to FIG. 15.

FIG. 17 is a representative timing diagram for dispensing plural doses of medication.

Figure 12:
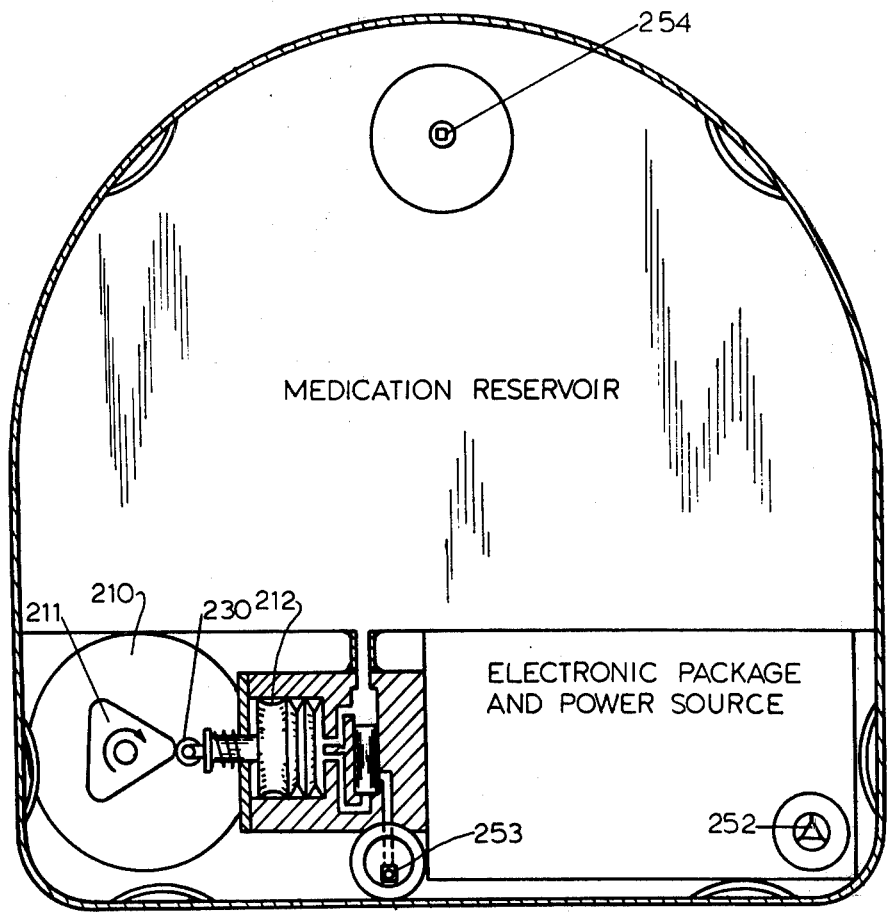
FIG. 12 is a schematic diagram of the apparatus of the invention as it might be used with supraventricular tachycardias treated with quinidine.
Figure 13:
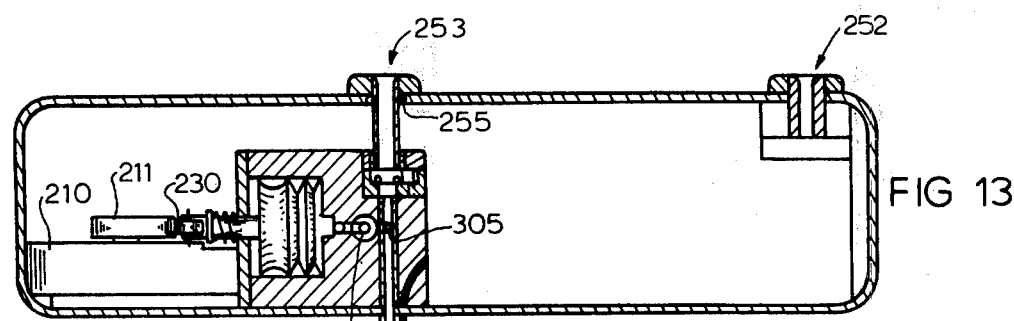
FIG. 13 is a schematic sectional view through the apparatus of FIG. 12.

FIG. 18 is a schematic representation of a needle connector-rotary switch arrangement illustrated in FIGS. 12 and 13.

Figure 19:
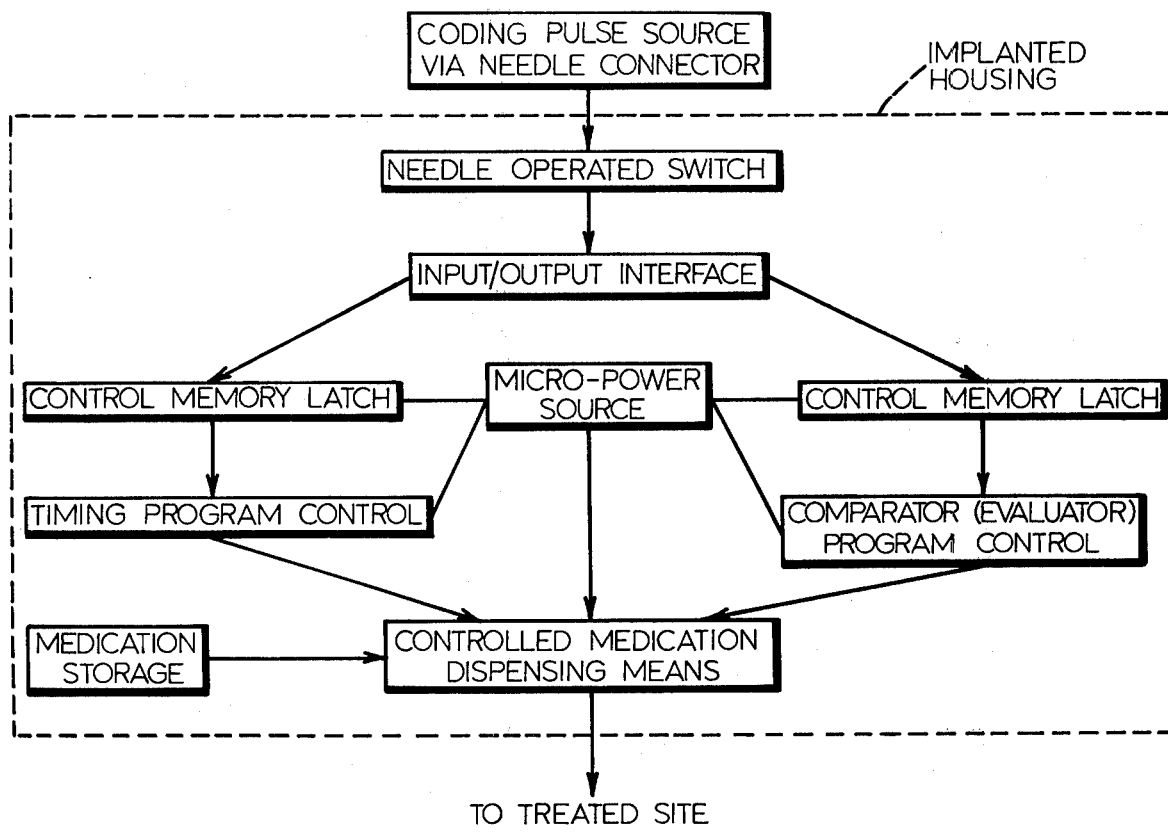

FIG. 19 is a block diagram illustrating how the needle-operated switch arrangement of FIG. 18 may be employed to modify the programmable characteristics of the control circuit.

Figure 20:
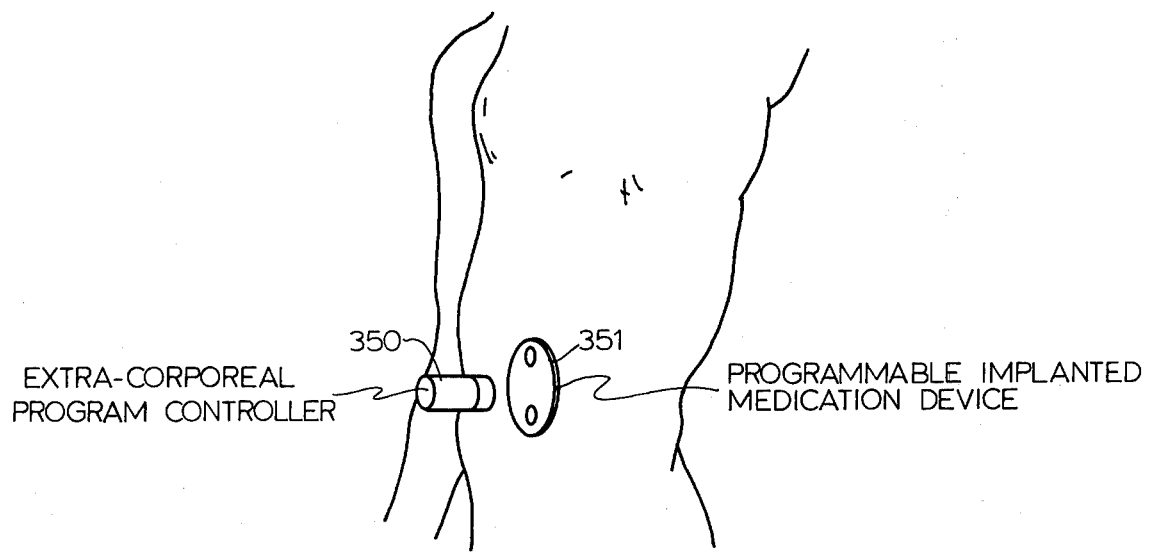

FIG. 20 is a schematic illustration of an embodiment using a pulse transmitter as a program control device and an implanted device controllable by pulse transmission.

Figure 21:
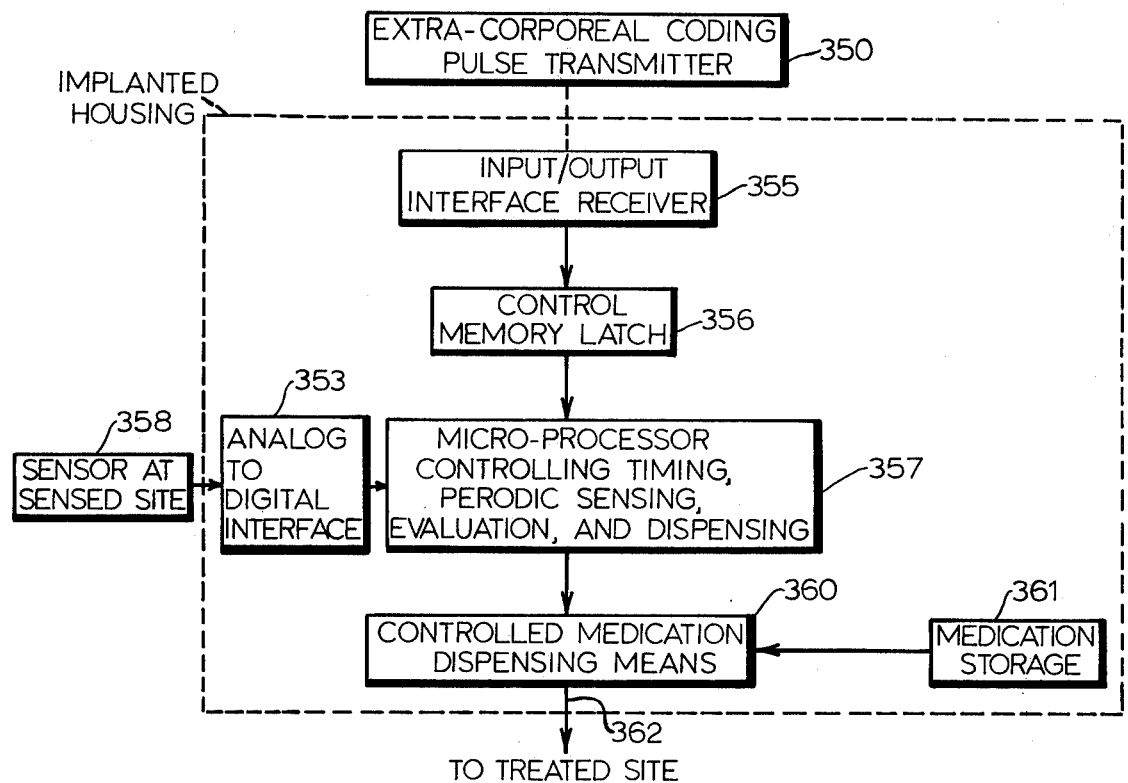

FIG. 21 is a block diagram illustrating use of pulse control for programming.

Figure 11:
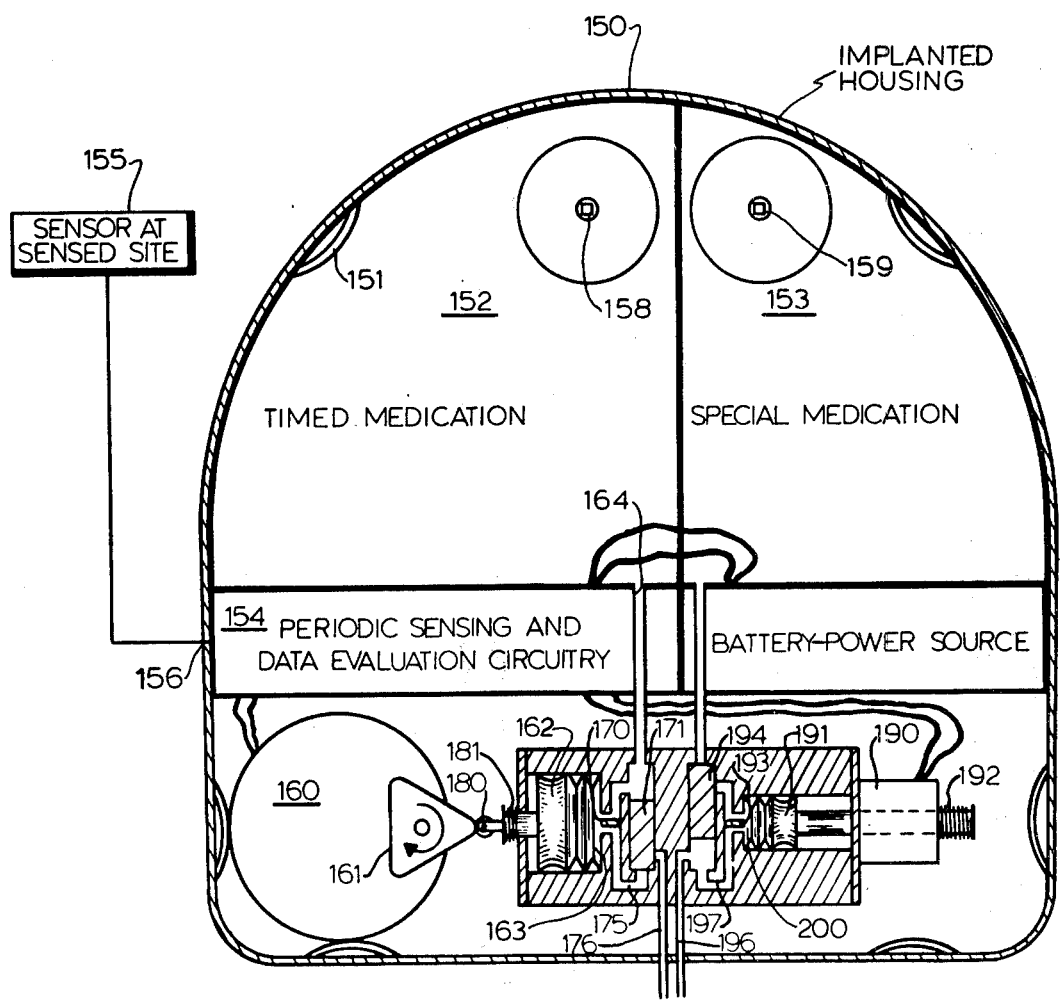
FIG. 11 is a somewhat schematic enlarged view of an implantable system according to the invention and adapted to dispense different medications from different sources under different controls.
Figure 22:
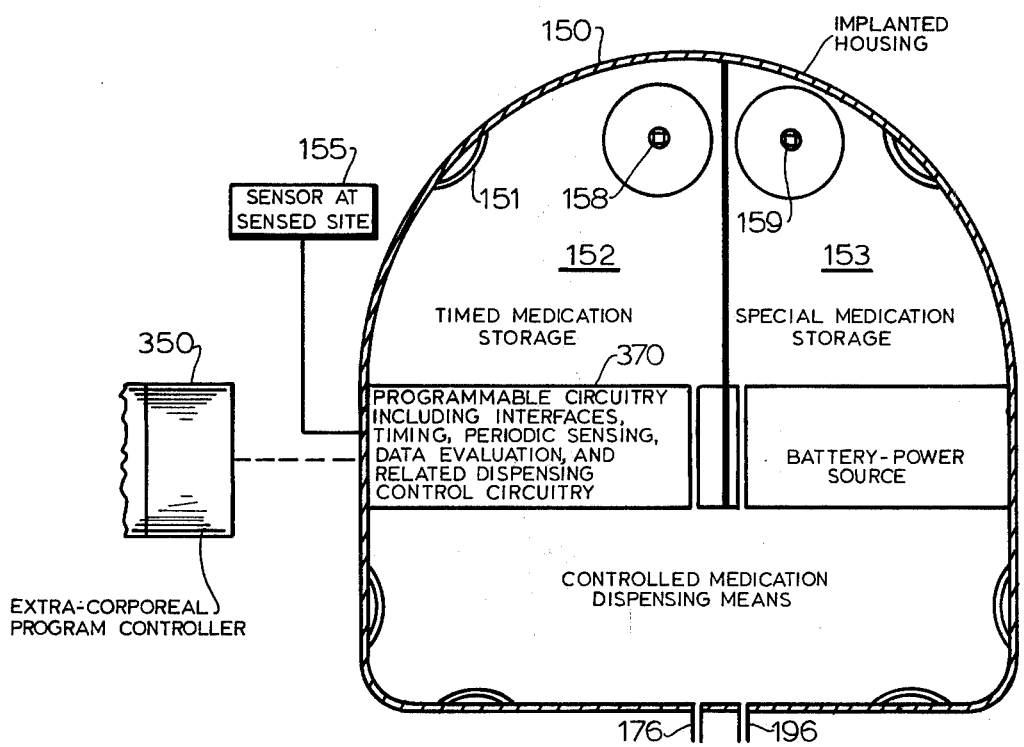

FIG. 22 is similar to FIG. 11 but illustrating use of pulse control.

Figure 23:
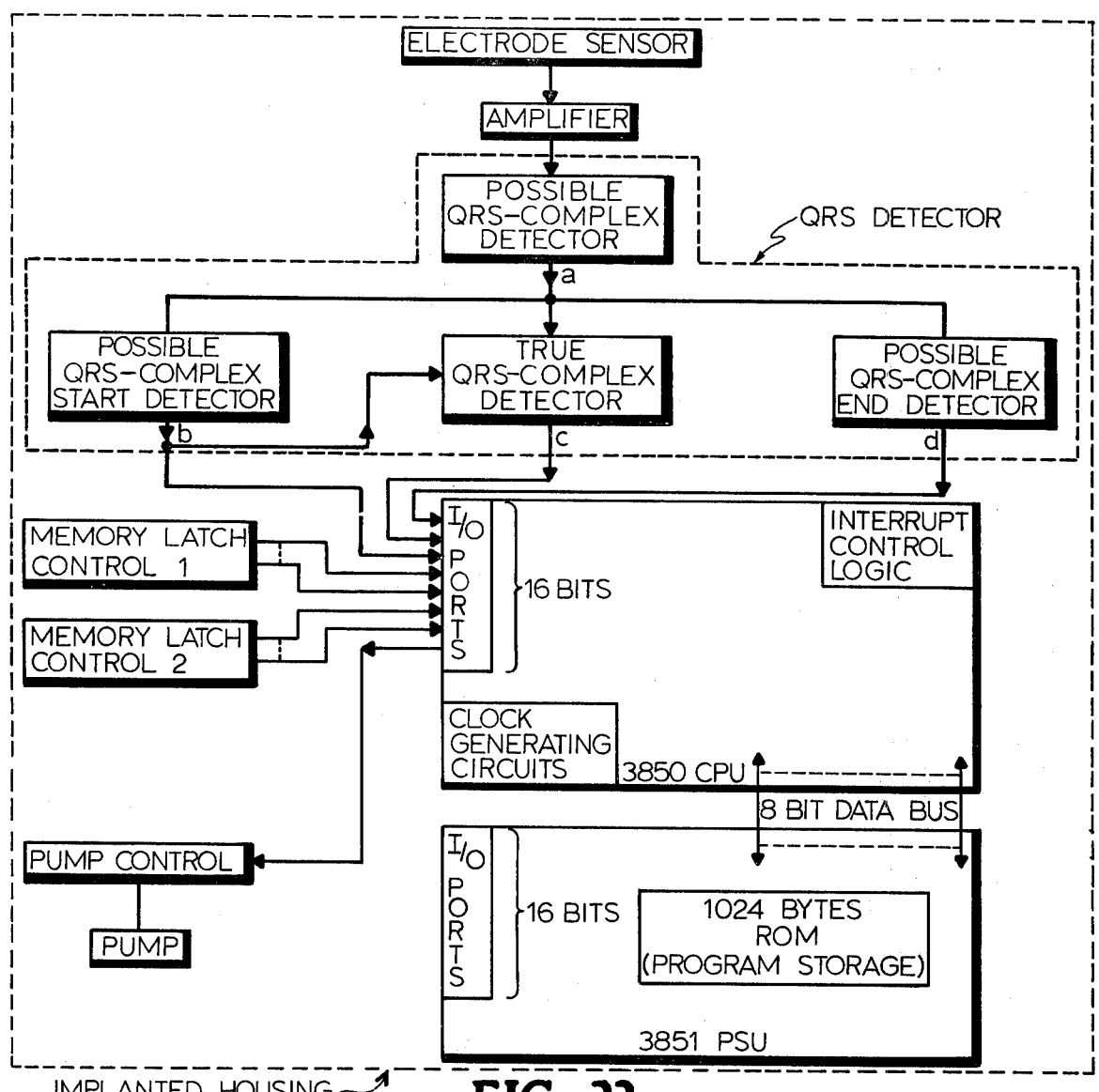

FIG. 23 represents a circuit similar to FIG. 16 but with the digital electronics of that system replaced by a microprocessor-type circuitry.

Figure 24:
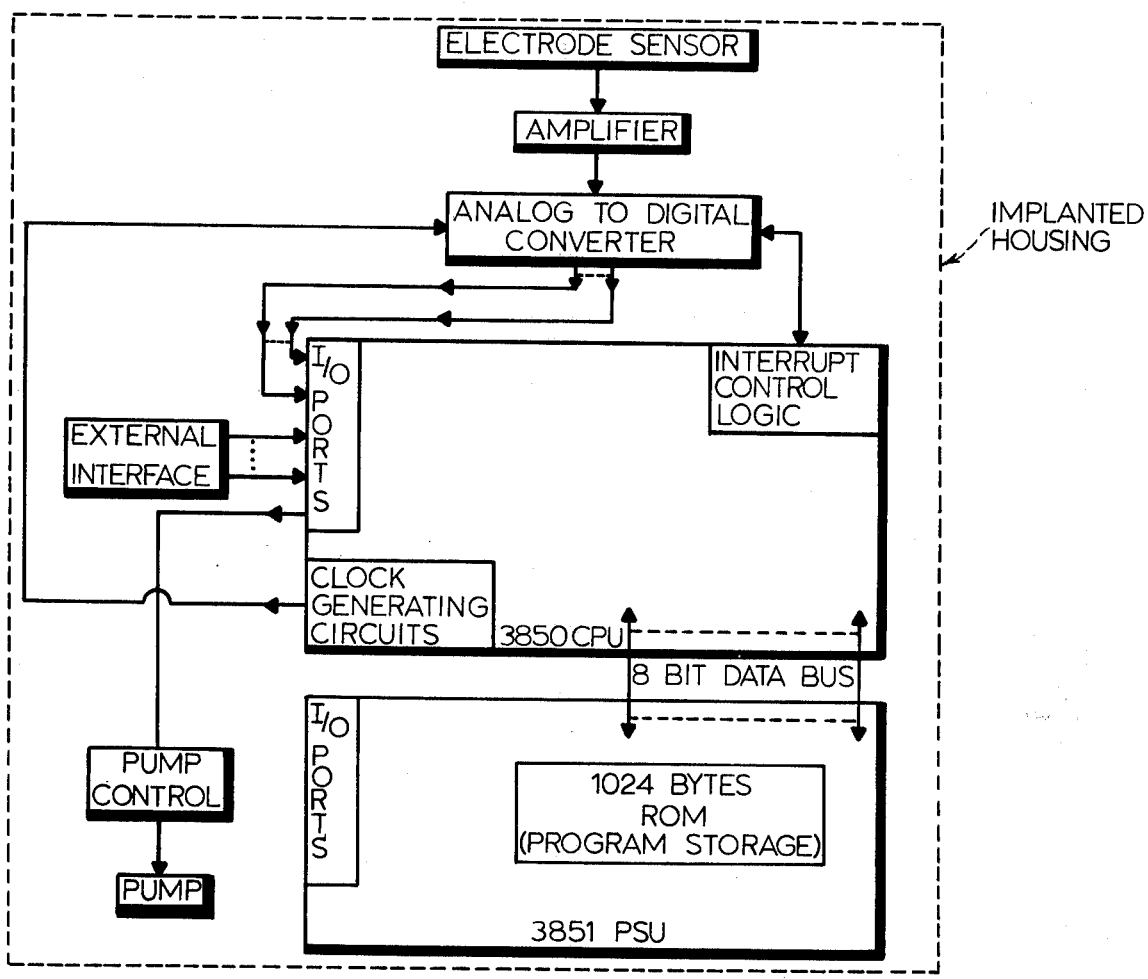

FIG. 24 represents a circuit similar to FIG. 23 but in a more advanced state in which the entire discrete electronic control system of FIG. 16 is replaced by a microprocessor system arranged to receive information through an analog to digital converter.

Figure 25:
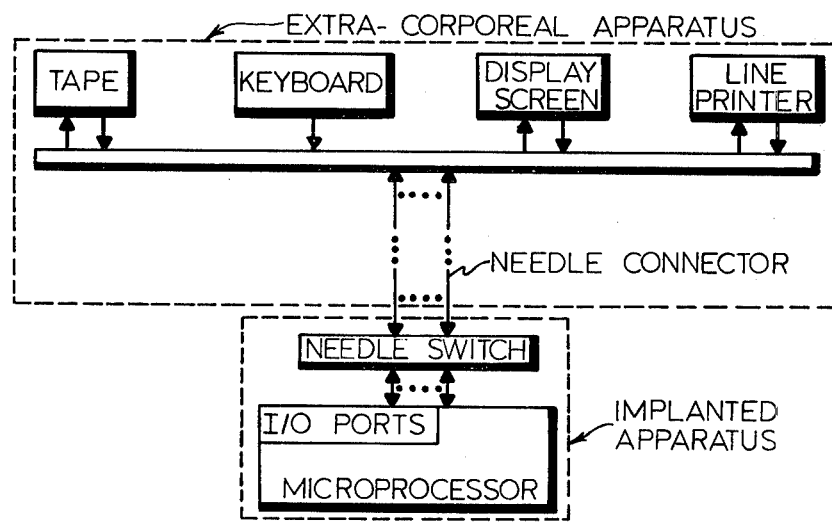

FIG. 25 is a schematic block diagram illustrating various forms of communication through the needle switch arrangement of FIG. 18.

Figure 26:
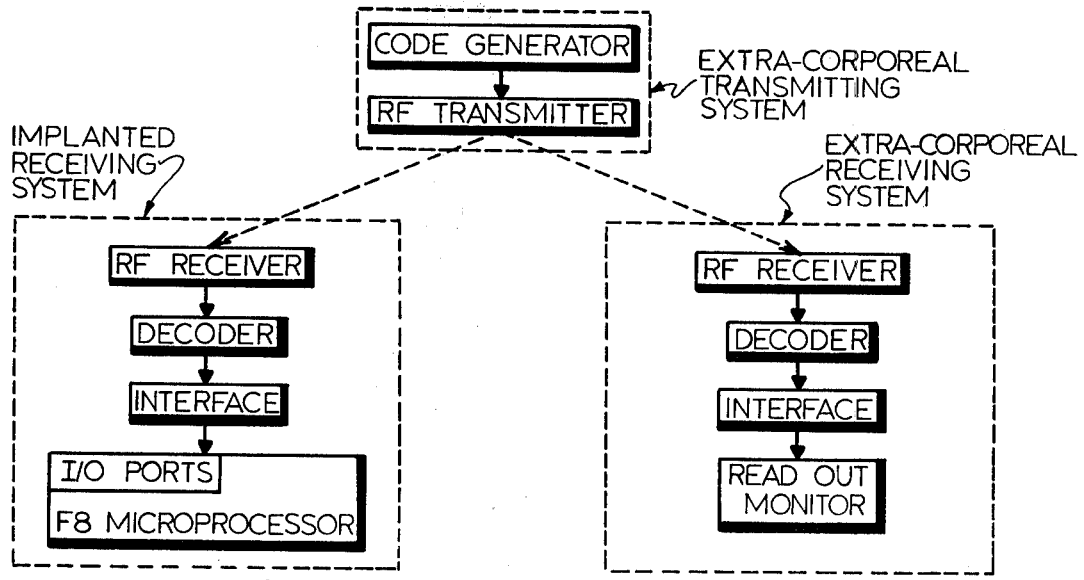

FIG. 26 is a schematic diagram of a system providing RF pulse code communication with both the implanted microprocessor control circuitry and an external receiver for monitoring the information transmitted.

Figure 27:
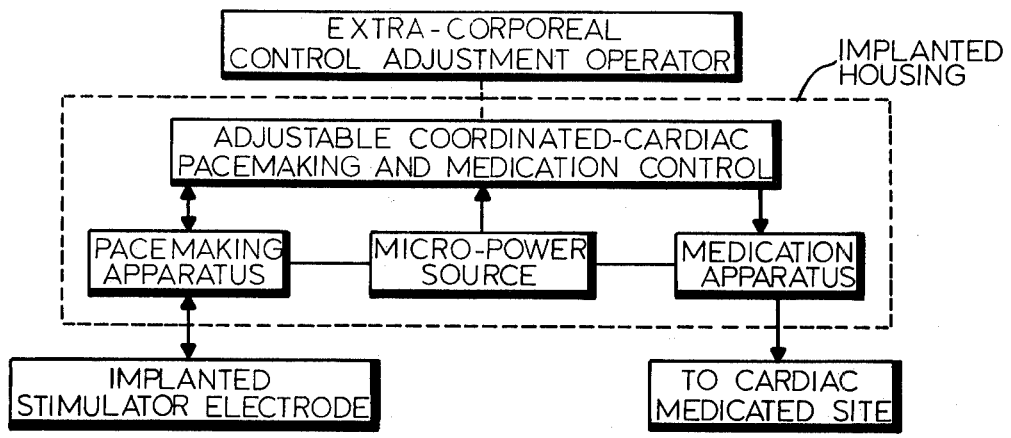

FIG. 27 is a block diagram broadly illustrating the combining of pacemaking and medicating activities.

Figure 28:
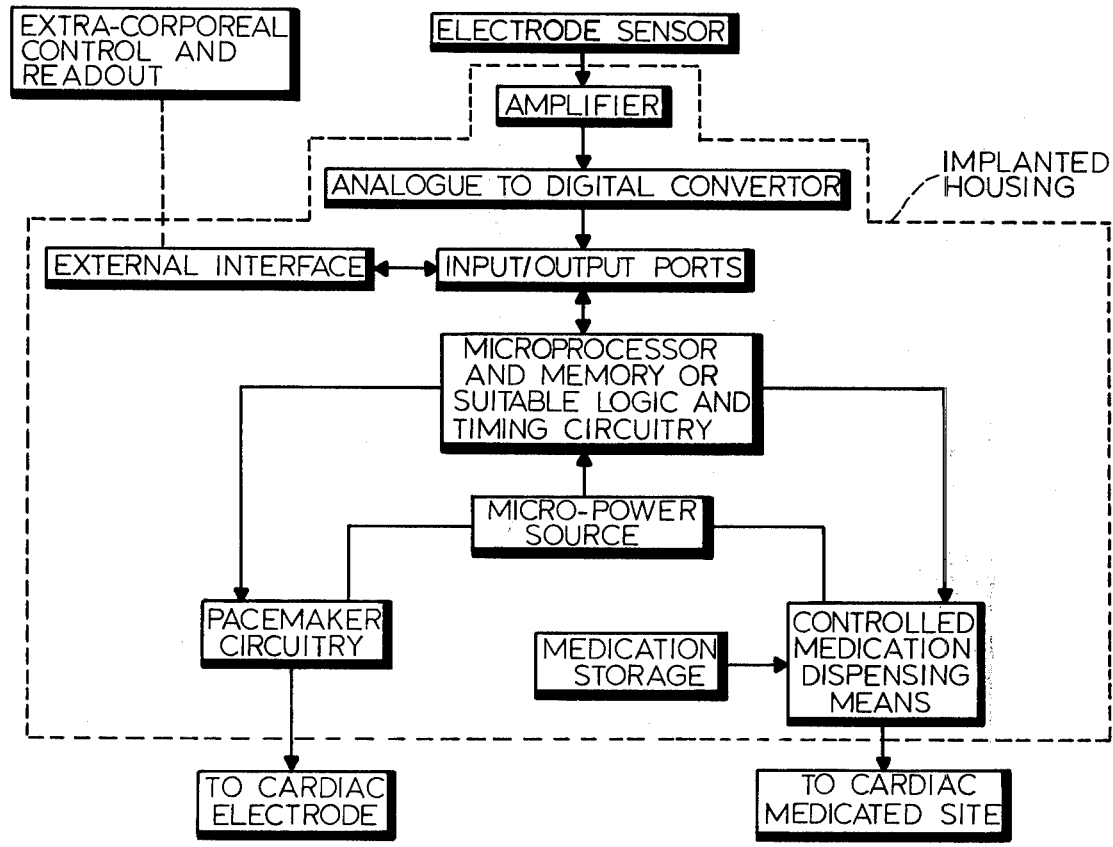

FIG. 28 is a more detailed block diagram illustrating a system having both pacemaking and medicating capability.

DESCRIPTION OF THE PREFERRED EMBODIMENT

Substantial background information has been set forth in my prior U.S. Pat. No. 3,692,027 and also in my copending application Ser. No. 463,262, now U.S. Pat. No. 3,923,060, and to which reference should be made in understanding the present invention. Of particular interest to the present invention, such background information indicates the very substantial number of conditions in the patient which are subject to change and which control both the need for medication as well as the kind of medication. Such conditions also are shown in the mentioned background information to dictate the program or schedule best suited to dispensing medication into the body.

In order to best understand the subject matter being claimed and which is of particular interest to the present application, the description related to the subject matter of FIGS. 1-17 and which appeared in the copending application Ser. No. 463,262, now U.S. Pat. No. 3,923,060, will be repeated. Thereafter, the description will be directed to describing the programming capability which is the particular subject of this application in reference to FIG. 16 and then there will be described the more advanced programming method and system capability illustrated in FIGS. 18-26. The subject matter of FIGS. 1-17 will then be seen to be applicable to both a nonprogrammed as well as to a programmed type implanted system and method of medication.

Figure 1:
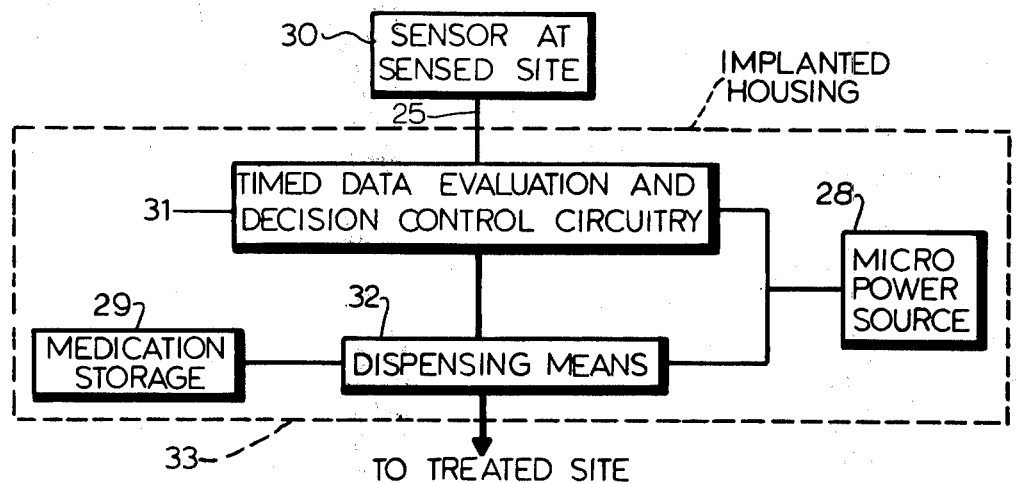
FIG. 1 is a block diagram illustrating the basic components of an apparatus according to the invention.

FIG. 1 illustrates in block and schematic diagram form the basic components of an implantable system according to the invention. In particular, there is provided a micro-power source 28, a medication storage 29, a sensor 30, a connector 25, a dispenser control 31, and a dispenser 32. All of the components except sensor 30 are contained in an appropriate housing 33 which is implanted in the body of the persons being treated. Power for the system is provided by a suitable micropower source 28 such as described in U.S. Pat. No. 3,692,027. The purpose of the sensor 30 in each instance is to sense some type physiological, chemical, electrical, or other condition in the body at a particular site, and produce data which corresponds to the sensed condition at the sensed site. This data, according to the invention method, is then sampled and evaluated by an appropriate dispenser control 31, e.g., a logic circuit, and depending on whether the sensed data is or is not indicative of a need for medication, the dispenser control 31 will operate in a manner to cause the dispenser 32 to either remain off or to be operated to dispense some predetermined amount of medication from the storage 29 according to the patient's needs.

Figure 2:
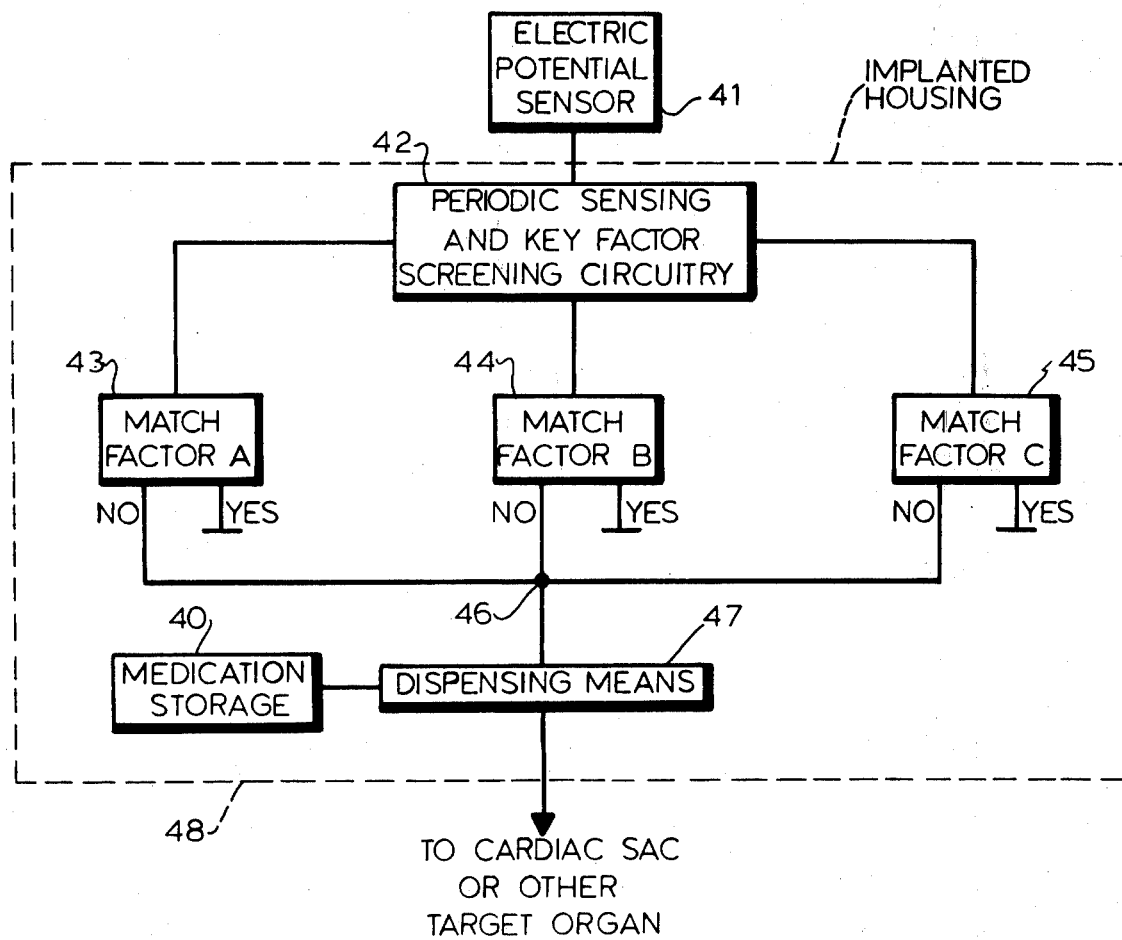
FIG. 2 is a block diagram illustrating the application of the invention to cardiac monitoring and medication.

Referring next to FIG. 2, there is schematically illustrated a more specific and somewhat more complex application of the invention to cardiac monitoring and medication. The micropower source, while not shown for simplification, should be treated as part of the FIGS. 2-6 systems. In the application of FIG. 2, there is provided medication storage 40 and an electric potential sensor 41, such as employed in electroencephalogram and electrocardiogram examinations. While indicated as a single sensor, sensor 41 could comprise plural, e.g., two or more, sensors. The sensed information is directed to an appropriate logic circuit 42 which is designed to screen the sensed data for key factors. Since logic circuits as such are known and within the skill of the art to design, the description in general will speak more to the medical aspects than to the precise details of the circuitry, although a more complete circuit disclosure will be provided in one example to be presented later.

With further reference to FIG. 2, it is known that sensed electric potential data such as obtained in electroencephalogram and electrocardiogram examinations will reveal a plurality of factors. The assumption on which FIG. 2 is based is that there are three factors A, B and C, which can be screened out and matched in appropriate subsidiary logic circuits 43, 44, 45 against normal limits. For example, subsidiary circuit 43 can match factor A as to whether it is or is not within normal limits (WNL) and produce a "no" or a "yes" output accordingly. Subsidiary circuits 44 and 45 can be designed for similar functions with respect to factors B and C such that if factors A, B and C are all outside normal limits an output is produced at junction 46 and which can be used to control the dispenser 47. Other combinations are possible. All of the components except the sensor shown in FIG. 2 should be noted as being enclosed in a suitable implantable housing 48.

Figure 3:
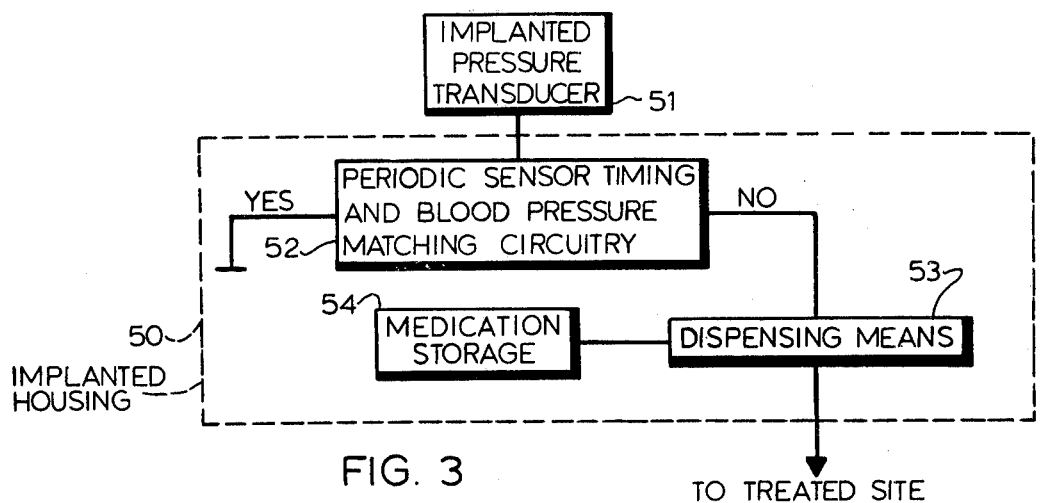
FIG. 3 is a block diagram illustrating the application of the invention to blood pressure monitoring and medication.

To illustrate a further application, reference is made to FIG. 3 which is directed to a blood pressure monitoring and medication system. In this application, there is provided a pressure transducer 51 which is connected to an appropriate logic circuit 52 contained in an implantable housing 50 and which is designed to make decisions on the basis of systolic and diastolic characteristics. If the blood pressure is not within the defined limits a "no" output is produced and which is used to operate a suitable dispenser 53 having medication selected from storage 54 to reduce the pressure.

Figure 4:
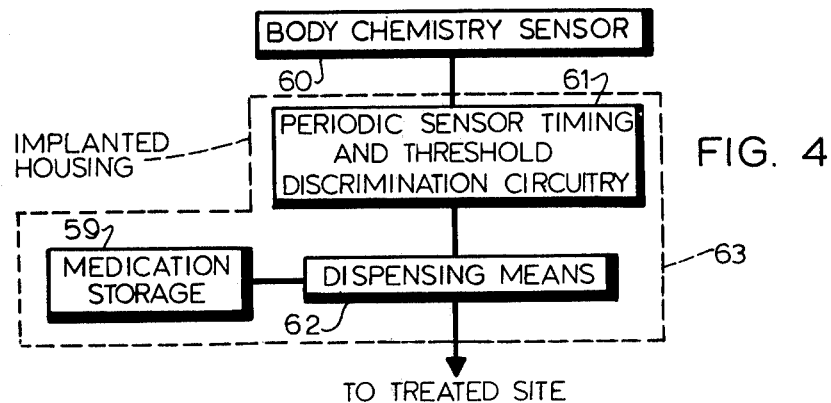
FIG. 4 is a block diagram illustrating application of the invention to body chemistry monitoring and medication.

In FIG. 4 a chemical monitoring system is illustrated. In this embodiment, a suitable chemical level sensor 60 is employed and which, for example, may sense pH changes, ionic changes, glucose level or other body chemistry factors susceptible to sensing. The sensor 60 is connected to an appropriate threshold discriminator and logic circuit 61 which in turn is connected to a medication dispenser 62 and all of which components except the sensor are contained in a suitable implantable housing indicated by 63 which also houses the storage 59. In this application, the logic circuit 61 determines whether the sensed chemical factor is or is not within an acceptable threshold and, if not, operates the medication dispenser 62 to bring such factor within an acceptable threshold.

Figure 5:
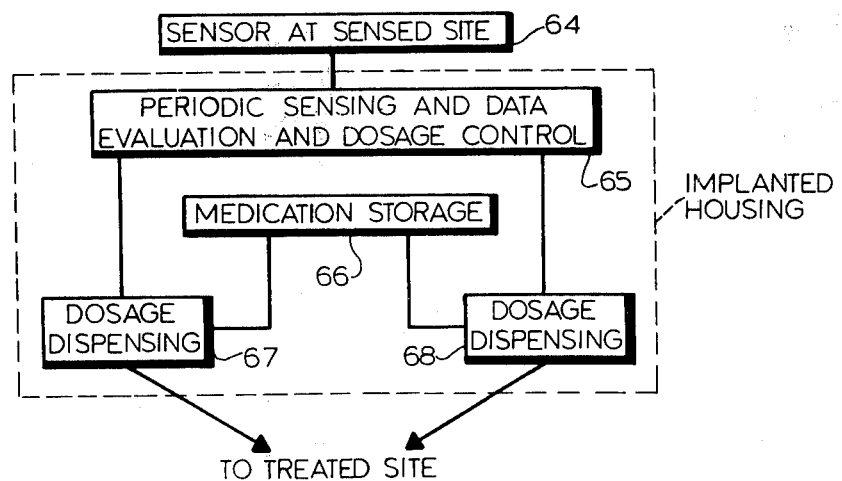
FIG. 5 is a block diagram illustrating application of the invention to dispensing medication to the same site from multiple sources.

Making reference next to FIG. 5, there is shown in block diagram form an application of the invention wherein dosages of the same medication may be dispensed from different sources. In this embodiment, the sensor 64 is connected to appropriate logic circuitry 65 which controls periodic sensing, evaluation of the sensed data and dispensing of medication from a common medication storage 66 through a dispensing means 67 or a separate dispensing means 68. For example, dispensing means 67 may constitute a low volume, regularly dispensed medication whereas dispensing means 68 may be used for supplementary medication at the same treated site.

In FIG. 6, the sensor 70 is connected to the appropriate logic circuit 71 which controls a dispensing mechanism 72 for dispensing from a drug storage 73, having, for example, drug A. Circuit 71 also controls the dispensing mechanism 75 for dispensing from an alternate drug source 74, for example, drug B. In this application it can be seen that different medications can be dispensed to the same or different treated sites with one medication being for one purpose and another medication being for another purpose. Housing 76 encloses the apparatus.

From the foregoing description, it can be seen that the various applications of the invention will each require appropriate timing and sensing devices, appropriate circuitry for evaluating and making decisions about the sensed data, and appropriate dispensing devices for dispensing medication subject to the evaluation of the sensed data. Implantable sensors for a great variety of purposes are well known and those skilled in the art will quickly appreciate their applicability to the broad concept embodied in the present invention. Those skilled in the art will also readily ascertain other types of implantable sensors which are suited and the required parameters for other types of sensors.

Considering next the type of logic circuitry required, given the concept of the invention, the design of such will be readily apparent to those skilled in the art. In general, the logic circuitry will be of a type in each application suited to receiving sensed data from a sensor, e.g., a transducer, in a form corresponding to the particular application, e.g., pressure data, chemical data, electrical data, et cetera, and producing an output depending on the data evaluation. In some instances, as previously noted in connection with FIG. 2 there may be a plurality of output data on a single output which can be screened by different subsidiary circuits for different data, e.g., factors A, B and C, as in FIG. 2. Miniature logic circuits of the kind required by the present invention may be found in both electronic design books as well as in medical literature, e.g., designs for demand pacemakers. Those skilled in the art will also readily appreciate the fact that the present invention is of such wide scope that the logic circuit designer is given a wide choice in the types of circuitry which may be used to perform the logic functions.

Another important consideration concerns the implantability of the sensor employed, the implantability of the housing which houses the medication storage and dispensing apparatus and the implantability of any catheter or other device employed to discharge the medication at the treated site. Since sensors, particularly electrical sensors, long term implanted diffusion devices, and the like, have all been used and the implanting problems are well known, the parameters required for implanting are considered known to those skilled in the art. Also, since pacemakers have been implanted, the general parameters for implanting a housing of the type required by the present invention is also well known. The long term discharge of medication internally through implanted catheters, and the like, fed by external sources of medication is also a current practice. Thus, tissue growth problems, tissue blockage problems, and the like, of the kind encountered in prior practices are contemplated by the present invention and the same technology previously developed will be useful in the present invention.

Each application of the invention requires means for storing a treating substance, preferably under pressure, in powdered, liquid, or other dispensable form, means for pumping or otherwise removing predetermined portions from such storage and means for directing the measured dosage to the appropriate organ or site best suited to receiving the dosage. The amount of pressure may vary with the medication because of different viscosity, dose sizes, etc., and many arrangements known in the pumping art will suggest themselves. For example, the medication may be enclosed in an elastic sack and forced out by introducing an inert gas within the storage area to assert pressure.

The most immediately available device suited to the invention for storing and dispensing medication is illustrated in my prior U.S. Pat. No. 3,692,027. For example, such a device as shown in my prior patent may constitute the dispenser 32 illustrated in FIG. 1 and the dispenser control 31 in FIG. 1 may include a switch device connected so as to connect and disconnect the battery which is used to power the device of my prior patent. In this application, the sensor 30 of FIG. 1 senses the particular condition at timed intervals and the dispenser control 31 of FIG. 1 causes the dispenser mechanism, such as illustrated in my prior patent, to either operate or not operate according to the evaluation and decision based on the sensed data. Appropriate controls are preferably provided for in the circuit logic to prevent overdose if the sensed physiological change does not occur quickly enough in response to the medication dosage, e.g., appropriate timing delays or dose/time functions.

The invention readily lends itself to a variety of dispensing mechanisms. Mention has already been made of the mechanism described in my prior U.S. Pat. No. 3,692,027. Another mechanism for pumping fluid medication is shown in FIG. 7. In FIG. 7 there is shown in a highly enlarged form a housing 80 mounting a piston 81 secured to a bellows container 82 made of a polymer or other suitable material. A rod 83 attaches to piston 81 and is caused to move inwardly by an appropriate solenoid 84 and to move outwardly by an appropriate spring 85 acting against a head portion 86 as schematically represented in FIG. 7. Solenoid 84 is, of course, controlled by an appropriate logic control as previously explained. The bellows 82 receives medication through an inlet tube 87 and a one-way valve 88 and discharges such medication through a one-way valve 89 and a discharge tube 90. It should, of course, be understood that the pump structure shown in FIG. 7 will in practice be contained in the implanted housing previously referred to and has the particular advantage of not requiring a high friction producing seal between piston 81 and housing 80 since all medication will be sealed and confined to the interior of bellows 82. Bellows pumps as such are known and proven.

One problem common to many types of physical disabilities is the need to dispense a daily average dose e.g., insulin, on a regular basis and to dispense intermittently dosages of short acting drugs, e.g., insulin, when need arises. FIG. 8 schematically represents a device suited to this requirement. In particular, cam 100 is driven by a suitable micro power motor such as shown in my prior U.S. Pat. No. 3,692,027 and which is arranged to be energized through an appropriate logic circuit, not shown. Rotation of cam 100 engages roller 101 and forces arm 102 to move piston 103 which causes the bellows 104 to discharge from the drug storage area 105 a predetermined dosage previously obtained from a drug storage 106. As cam 100 rotates and after discharge bellows 104 retracts and refills the chamber 105 at a suitable time the control for cam 100 causes it to stop. Appropriate one-way valves 107 and 108 control the intake and discharge. Such a cam driven arrangement may thus provide the required daily average dosages. For intermittent additional needs, a solenoid 110 is connected to the appropriate logic circuit, not shown, and when energized will move arm 111 and operate piston 112 to provide a lesser amount than is obtained by cam 100 so as to provide a smaller dosage. Solenoid 110 is de-energized at the end of the discharge stroke and spring 113 causes the storage area 114 to refill.

In FIG. 9 there is indicated an arrangement for discharging two different types of medication. In FIG. 9, cam 120 and solenoid 121 should be considered similar in their operation to the cam and solenoid operations previously explained in connection with FIG. 8. In the FIG. 9 application, the cam 120 operates on the bellows 123 and solenoid 121 operates on the bellows 124. In the FIG. 9, as well as in the FIGS. 7 and 8 dispensing arrangements, power for the respective drive members, e.g., rod 83, cam 100, is provided by the previously mentioned micro-power source. One type of medication, e.g., a long acting drug, may be stored in one storage reservoir 125 and a separate medication, e.g., a short acting drug, may be stored in a separate storage reservoir 126. Thus, one drug source may be dispensed by use of solenoid 121 and another drug source may be dispensed by the use of cam 120. It will, of course, be understood that appropriate one-way valves and other features of known mechanical construction may be employed even though not shown or specifically explained.

Figure 10:
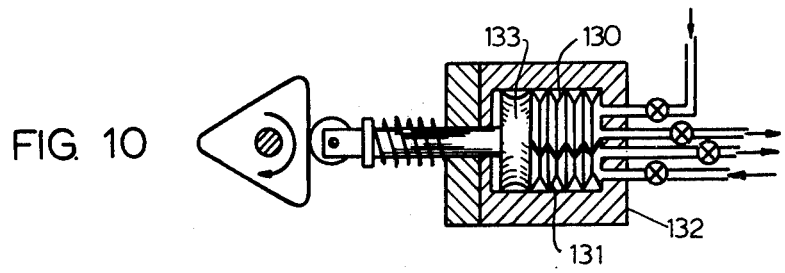
FIG. 10 is a somewhat schematic enlarged drawing of a bellows pump with multiple separated chambers for different chambers or sites having a common power source.

In FIG. 10 there is shown a reservoir arrangement comprising a bellows with two compartments 130, 131 housed in a common housing 132 and operated by a plunger piston 133. From the drawings, it can be seen that this arrangement, like that shown in FIG. 9, provides for dispensing two or more types of medication to two or more body sites. The FIG. 9 arrangement allows such medication to be dispensed to two sites at different pressures using two power sources whereas the FIG. 10 arrangement provides for the medication to be dispensed to two or more sites at unequal pressures using only one power source. In addition, the multiple chamber bellows of FIG. 10 provides for a two or more drug dispensing capability without the greatly increased friction of more cylinders and pistons. The bellows chamber in addition to its sealing functions allows for a variety of options at the time of implanting surgery simply by substituting various bellow configurations in the pump. This means that the surgical facility does not have to maintain many types of more expensive total pump configural changes. It is anticipated that a large variety of bellow shapes and sizes will be found useful and which can be substituted in the pump cylinder for a multitude of treatment purposes.

In FIG. 11 there is schematically shown a system of a type which corresponds with the type of application diagram in FIG. 6. Here again it should be understood that the schematic diagram in FIG. 11 would, in practice, correspond to a device of substantially less physical size. In particular, there is represented in FIG. 11 a housing 150 having appropriate suture anchors 151. Within the housing 150 there is provided an appropriate compartment 152 for holding some predetermined amount of medication intended to be released over a long term for a chronic situation requiring regular dosages whose size can be predetermined and scheduled. The compartment 153 represents a storage area for special medication such as might be required by unusual and transient conditions in a specific patient. The previously mentioned evaluating and control circuitry is indicated as being confined in a separate compartment 154 and which is connected to an appropriate sensor 155 located within the body being treated but external of the housing 150 and connected through suitable housing wall opening 156. For the timed medication a micro-powered unit 160 of the type shown in my prior U.S. Pat. No. 3,692,027 is controlled by the circuitry in compartment 154 and when indicated by evaluation of information coming from sensor 155, unit 160 turns on and rotates the cam 161 thus driving the cam peaks against roller 180 attached to the shaft of piston 162 so as to discharge the medication confined in the storage area 152 through an appropriate discharge tube 164. During discharge the flap valve 170 closes as piston 162 moves to the right in FIG. 11 and a sliding cylindrical valve member 171 moves upwardly in FIG. 11 so as to allow communication between pipes 175 and 176. As cam 161 continues to turn roller 180 continues to ride on cam 161 by reason of spring 181. Flap 170 opens, sliding valve 171 moves down and a new charge is stored in the storage area 163. Portals 158, 159 provide for refilling.

When there is a demand for special medication as determined by sensor evaluation with the logic circuitry in compartment 154, solenoid 190 is energized which causes piston 191 to move to the left in FIG. 11 against the tension of spring 192. Flap valve 193 closes, sliding valve 194 rises as shown in FIG. 11 and pipes 195 and 197 are placed in communication to allow discharge through pipe 196. On the return stroke, sliding valve 194 moves down, flap valve 193 opens and a fresh charge of the special medication is drawn into the storage area 200. Thus, by energizing and de-energizing the power unit 160, the treated body can be provided with the periodic-timed medication and by energizing and de-energizing the solenoid 190, the treated body can be provided with the special medication.

There is next given a more detailed disclosure directed to a cardiac pump mechanism to dispense medication for prevention of recurrent tachycardias. As background, it should be noted that quinidine is given on a chronic basis for the prevention of recurrences of atrial fibrillation and flutter as well as supraventricular tachycardias not due to digitalis toxicity. Quinidine is also effectively used, as well as procainamide, in prevention of recurrences of ventricular tachycardia. Quinidine is also used to prevent recurrences of ventricular fibrillation except when ventricular fibrillation occurs during complete heart block in which case it is contraindicated. A discussion of treatment of cardiac arrhythmias can be found in "Drugs Used in the Treatment of Cardiac Arrhythmias" in Treatment of Heart Disease in the Adult, 2nd Edition, Rubin, T. L.; Gross, H.; Arbeit, S. R., Lea and Febriger, Philadelphia, pp. 297–324, 1972. One of the difficulties in using these drugs is that the therapeutic index, the ratio of therapeutic dose to toxic dose, is quite low. The pump feedback system of the invention is, however, adapted to carefully monitor the state of the heart and toxic manifestations of the drug and maintain the drug dosage at a level designed to minimize, if not eliminate, complications attributable to the medication. Thus, the device and method of the invention allows more general use of these medications in what are quite severe and life-threatening conditions of the heart. The invention is directed to what is needed, namely, a feedback evaluation system that will provide for the maximum needed therapeutic dose that can be maintained below the toxic manifestations of the drugs.

The described goals can be accomplished by monitoring the disease condition and regulating the medication to treat the condition according to the invention and yet steering clear of the toxic manifestations of the drug by monitoring and regulating the dose in relationship to these manifestations also. The disease entity to be treated as an example is the supraventricular tachycardias. The present example is directed to counterpointing the heart rate against the toxic changes produced by quinidine, that is widening of the QRS complex (a component of the electrocardiogram). The dose of quinidine can thus be monitored by use of the invention and reduced when there is prolongation of the QRS complex which occurs as the dose of quinidine begins to reach threshold for toxic effects.

FIGS. 12 and 13 demonstrate the basic construction and operation of the device to be used with supraventricular tachycardias treated with dispensed quinidine. The pump motor 210 is of the type shown in my U.S. Pat. No. 3,692,027 and is set to turn the equilateral cam 211, e.g., eight or more revolutions per day, thus providing a total of 24 potential cam pump activating contacts with the roller 230 which operates piston 212. Thus, the pump can potentially operate every hour of the day providing for 24 potential doses per day. Using this paradigm provides the following options, if one operates on a two-hour dispensing schedule, that is dispensing medication every two hours unless altered by decisions based on evaluation of the sensors (the two-hour schedule is accomplished by turning off the pump motor 210 every other hour): 1. The mechanism would dispense every two hours as an average dose timing. 2. Depending on the feedback evaluation, it may suppress a dose of medication for two hours thus leaving a four-hour interval between doses when this is indicated. 3. Extra doses can be dispensed on a one-hour schedule if needed. In actual operation, the movement of pump motor 210 will turn the cam 211 and dispense the first dose. Then the timing mechanism cuts off the mechanism for one hour unless conditions require that an extra dose of medication be provided and in this case the mechanism is designed to continue to operate for the next hour to provide an extra dose. Thus, under normal operating conditions, the mechanism will provide 12 daily doses every two hours. Should toxic conditions of quinidine manifest themselves, then the mechanism may be cut off for sufficient time to increase the interval between medications to four hours.

In actual practice with a supraventricular tachycardia, the electrodes 250 shown in FIG. 13 on the heart itself pick up electrical activity of the heart and conduct the heart signals to amplifiers in the electronic package by wires 251 embedded in the catheter 248. An electronic logic recognition program provides for identification of the QRS complex and another program subsequently quantifies the QRS period and R-R interval as described in relation to the chart shown in FIG. 17. Operationally, the cardiac frequency (R-R interval) is monitored and averaged for each hour over the 24-hour period and stored in a register. The lowest frequency average for an hour during the 24-hour period is compared with the lowest frequency hour from control periods as to whether this has increased by 10 to 20 percent over criteria control levels which criteria are set at time of implantation. Thus, if the frequency has increased by 20 percent, then the mechanism will provide three extra one-hour doses every 8 hours for the next 24 hours. The decision-making control logic in the system provides for this operation. The contrasting concern, that of quinidine toxicity, is monitored by the QRS period. The QRS period is sampled and evaluated each hour and if it increases over criteria levels (% of control) or if premature ventricular contractions develop (indicated by very wide QRS complex over 150% of control) especially with the quinidine effect controlled, then the next dose period is suppressed by cutting off the power to the pump motor 210 and secondly stops the extra dose for that 8 hour period that is currently operational because of the criteria provided for in the first series of feedback options.

The chart depicted in FIG. 17 is explained as follows:
Condition I = Normal operation-pump operates every two hours on even hours.
Condition II = Cardiac frequency has increased by 10–20% which actually means the R-R interval has decreased by 10–20%. In practice, the hour with the lowest frequency for the previous 24 hour day is compared with the control value to make this decision. Then, if this 24 hour lowest hour frequency is 10–20% higher than control, the logic provides for three extra doses the next day given every 8 hours at 1, 9, and 17 hours.
Condition III = The sampled QRS period over the past hour is greater than criterion levels on the following basis; the QRS complex period is sorted on the basis of percent of control value and given a weight in the following schedule:
(1) 110% or less than control value given weight of zero
(2) 110–120% greater than control value given weight of one
(3) 120–130% greater than control value given weight of two (4) 130–150% greater than control value given weight of eight (5) Greater than 150% of control value indicates ventricular premature contraction and is given a variable weight of eight or sixteen. If over the hour, out of the 256 sampled QRS periods the weights add up to 256 or greater, then the pump is turned off for the next even hour operation and secondly stops the extra dose for that eight-hour period that might be currently operational because of criterion provided for in condition II. Thus, if the hour 4 dose was deleted, then the dose provided for at hour 9 would be deleted also.

Other aspects of FIGS. 12 and 13 that require explanation are the three input portals 252, 253, 254. Input portal 252 represents an eight position rotary switch and a needle contact access to which are obtained through the wall of the body. As schematically illustrated in FIG. 18, the rotary switch and needle contact operates by use of a solid core needle with a round to triangular to round O.D. (outside diameter) tip section which is inserted through the wall of the body and into portal 252 which has a mating triangular hole as shown. Operation of the switch is accomplished by turning the needle through one to eight of the various positions. Contact to the switch function is obtained through contacts on the three triangular surfaces of the needle approximated to the triangular hole contacts. The leads to the needle triangular surface are conducted down the long axis of the needle and are shielded by a suitable isoelectric material. In the example being used, position No. 1 of the rotary switch provides for battery recharge through the needle contacts. Position No. 2 provides for monitoring the electrocardiogram from the implanted electrodes. Position No. 3 provides for stimulation through the cardiac electrodes if pacemaking functions are needed. Position No. 4 provides for contact with the logic system for calibration of the logic of the cardiac response parameters. Position No. 5 provides for monitoring the logic output and number of doses per day. Position No. 6 provides for cutting off of the entire system. Positions No. 7 and 8 are for future options. Other types of needle-operated switches can be provided.

From the foregoing and later description, it will be seen that the invention provides an implanted medication system having stored medication, medication sensing means, circuitry for controlling the dispensing and means operable externally of the system for changing the character of the circuitry to change the manner of dispensing. While the present description deals with effecting changes in the circuitry by use of the described extracorporeal needle connector and implanted portal switch 252, later description deals with a system and method in which circuit changes are made through remote control and without requiring entrance through the wall of the body in which the system is implanted.

Catheter access portal 253 is a bypass catheter inlet and provides the following functions: (1) It allows the physician to exert increased pressure if mechanical block occurs in the catheter. (2) It allows the physician to introduce a wire stylet if mechanical block occurs in the catheter. (3) It allows the physician to introduce additional drugs into the pericardial sac if needed. The catheter access portal operates in a manner best explained by reference to FIGS. 14 and 14A. A hollow bore needle, not shown, with a round to square to round O.D. tip section is inserted through the patient's skin with the aid of protuberance 306 and thence into the square hole 303. The square needle segment engages the sides of the square hole 303. Rotating the needle about its long axis rotates pinion 302, which is meshed with and rotates partial ring gear 301. When partial ring gear 301 has rotated to its counterclockwise limit portal 307 is in line with the I.D. (inside diameter) of the needle allowing access to the catheter 304, and the pump output port 305. "O"-rings 308 and 309 seal the port in both open and closed configuration. Pinion 302 is held in position by top plate 310. In FIG. 14, the external casing of the device is represented by line 311.

For purposes of replenishing medication, the input portal 254 is employed. Since the introduction of pressurized replenishing medication has been previously discussed in my U.S. Pat. No. 3,692,027 and a suitable portal structure described, no further detailed description of this operation or of the refill portal is deemed necessary.

FIG. 13 shows in further detail the bypass system with the details of the attachment of the catheter system to the pericardial sac. O-rings 255 beneath the entry portal are provided for sealing purposes. A one-way valve 256 in the catheter leading to the pump provides for block of any increased pressure in the bypass system into the pump mechanism. The catheter system is sewn into the pericardial lining with a ring 247 embedded in the catheter 248 having both a uniform catheter section and an appended expanded catheter section in the form of a trumpet 249. The expanded catheter diameter provides for increased surface area and reduces any blockage due to the fibrosis around the exit portal to the catheter. Also shown adjacent catheter 248 are leads 251 leading from the pair of sensing electrodes 250 to the amplifier and logic system. These are actually embedded in the catheter and provide additional support for the catheter. The electrodes 250 and attached wires are embedded in a polymeric shield after their exit from the catheter.

Figure 13A:
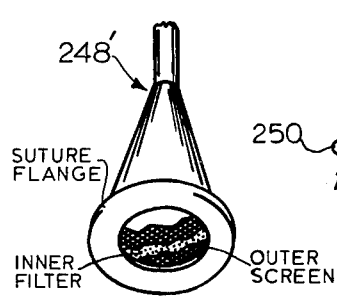
FIGS. 13A, 13B showing alternate catheters.
Figure 13B:
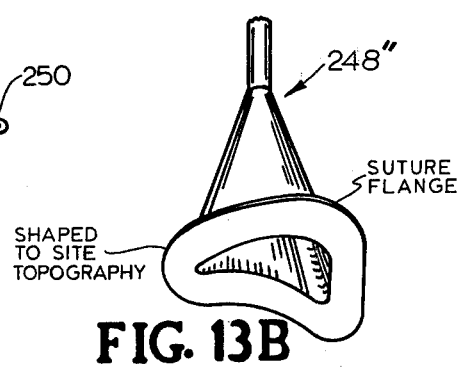

As illustrated in FIGS. 13A and 13B, an alternate catheter 248' (FIG. 13A) may include a suitable inner porous filter and and outer support screen to provide medication filtering and also to provide a barrier against entry of substances into the catheter. Another catheter form 248" (FIG. 13B) provides for the catheter to be shaped to the site topography to facilitate installation.

A block diagram describing the general operation and decision making involved in control of the cardiac medication pump is illustrated in FIG. 15. The depicted "electrode sensor" and "amplifier" are intended to represent standard devices such as are used in present cardiac pacemaker circuits. The remaining portion of the block diagram of FIG. 15 is the "brain" of the system and provides control to the "pump" based on the presence of conditions I, II or III, as previously described. The type and nature of components required for the FIG. 15 circuit are generally known and have been elsewhere indicated. Therefore, since FIG. 16 represents a more detailed description of FIG. 15, it is believed those skilled in the art will readily understand the circuitry and operation depicted in FIG. 15 after reading the description to follow.

The description now turns to a description of FIG. 16 which constitutes a logic circuitry suited to the application related to FIGS. 12–15 and 17. Since the components in FIG. 16 are identified and are known to those skilled in the art and their relation in the circuit is shown, the description will next concern itself primarily with the operation of the circuitry of FIG. 16. The "Possible QRS-Complex Detector" with output at (a) detects the beginning and end of all "possible" QRS-complexes. The start of a "possible" QRS complex is detected by the "Possible QRS-Complex Start Detector" with output at (b) and the end of a "possible" QRS-complex is detected by the "Possible QRS-Complex End Detector" with output at (d). The decision of whether the "possible" QRS-complex that is detected is a "true" QRS-complex is made by the "True QRS-Complex Detector" with output at (c). The outputs at (c) and (d) are then combined through an And Gate with output at (e). This output (e) represents the end of a "true" QRS-complex.

The QRS-complex is analyzed in two different ways: (1) Measurement of the time period of the QRS-complex; and (2) Measurement of the time period between two consecutive QRS-complex, i.e., R-R interval.

The measurement of the time period of the QRS-complex is accomplished through the "Percent Control-Time Classifier." The signal at (b) is the signal to reset and then start this classifier which classifies the time period of a QRS-complex into one of five time intervals: (I) 110% or less of control time, (II) 110% to 120% of control time, (III) 120% to 130% of control time, (IV) 130% to 150% of control time, or (V) 150% or greater of control time. The control time is the time period of a normal QRS-complex for the given patient. The signal at (f) occurs at the end of a "true" QRS-complex once every 256 times an hour. The pulse at (f) is the signal to add to the "Accumulating Counter For QRS Time Period." Depending on the percent of control time classification of the QRS-complex, this counter is incremented by 0, 1, 2, 4, 8, or 16 counts. Each classification adds a set number to the counter. Classification (V) has the additional option of having its count value changed to 4, 8, or 16 through "Memory Latch Control 1". This memory latch control can be set through the previously mentioned externally accessible rotary switch 252, not shown in FIG. 16 but shown in FIGS. 12 and 13 and also schematically illustrated in FIG. 19. If the count on the "Accumulating Counter for QRS Time Period" exceeds 256 in an hour then the output at (g) is a logic "one" otherwise (g) is a logic "zero".

Mention has been made of the use of an electronic recognition program to provide for identification of the QRS complex and of another program to subsequently quantify the QRS period and R-R interval in relation to the chart of FIG. 17. With this in mind, an aspect of the invention that should be recognized here is that the ability to set the Memory Control Latch 1, as just described, through the described needle connector and rotary switch 252, illustrated in FIGS. 12, 13, 18 and 19, gives the system and method of the invention what is effectively a simple and useful programming capability. That is, by being able to change the mentioned count value as well as the later described R-R Control Value with Memory Control Latch 2, the program character of the dispensing control circuit can be changed and thus the specific manner and conditions under which the medication is dispensed can be changed by means external of the system itself. In later description, a remotely controllable programmable medication dispensing control circuit arrangement which does not require manual switching or the use of a needle connector is explained.

To continue the explanation of FIG. 16, the measurement of the R-R interval is accomplished by the circuitry labeled "R-R Pulse Generator" which selects two consecutive "true" QRS-complexes once every 256 times an hour and outputs a logic "one" pulse at "h" equal in length to the time period between the end pulses of these consecutive "true" end pulses. This pulse at (h) is then gated through an And Gate with a 1000 Hz. clock and the resulting pulses at (i) represent the number of 1000 Hz. pulses occuring during a R-R interval once every 256 times an hour. These pulses at (i) are accumulated by the "R-R Interval Counter" with output at (j). At the end of each hour the contents of the "R-R Interval Counter" is compared with the "R-R Control Value". This control value represents the number of 1000 Hz. pulses that occur during a time period that is 20% less than a normal R-R interval for a given patient (i.e., a time period corresponding to a R-R frequency 20% faster than normal.) This control value is set through the previously mentioned externally accessible rotary switch 252 into "Memory Latch Control 2" as illustrated by FIGS. 18 and 19. If the hourly count is greater than the control value then the "present Day R-R Status" (which is normally a logic "one") is set to a logic "zero". Once set to logic "zero", it remains at logic "zero" for the remaining portion of the present day. At the end of the 24th hour this value is stored in the "previous Day R-R Status" for use in making the present day's pump decisions at the beginning of hours 1, 9, and 17. This output at (k) is a logic "zero" if any hourly R interval count for the previous 24-hour day was greater than the "R-R Control Value" for a given patient (i.e., if the average R-R frequency during any hour of the 24 hour day was slower than the 20% greater than normal control value).

The two outputs at (g) and (k) control the pump operation. Normal operation causes the pump to dispense at all even hours (Condition I in the FIG. 17 Chart). Increase in frequency for the lowest "hour frequency" for the 24 hour period of the previous day (indicating need for more medication), a logic "one" at (k), provides for the pump to dispense additional doses at hours 1, 9, and 17 (Condition II in the FIG. 17 chart). These two operations occur in the following manner: If either the output at (n) or (q) is a logic "one" then the input to the "Pump Control" is a logic "one" at (r). A logic "one" pulse at (r) is the signal to turn on the pump. This signal at (r) is a logic "one" at even hours (output (m)), normally, and at hours 1, 9, and 17 (output (p)) under Condition II of the FIG. 17 Chart unless these conditions are altered by one of the following restraints: If the output at (g) is a logic "one" for any hour then the output of the "Two Hour Memory" at (1) is set to a logic "zero" for the next two hours (normally this output at (1) is a logic "one"). This signal (1) is gated with the even hour pulse at (m) through an And Gate with output at (n). If the output at (g) is a logic "one" for any hour then the output of the "Eight Hour Memory" at (o) is set to a logic "zero" for eight hours. (Normally this output at (o) is a logic "one") This output at (o) is gated with the logic "one" pulse at hours 1, 9, and 17 at (p) and the pulse at (k) through an And Gate with output at (q).

With the foregoing in mind, it should be noted that the power unit 210 of FIGS. 12–13 and which is associated with the FIGS. 15–16 circuitry, is appropriately geared to operate on a fifty minute hour in contrast to the 60 minute hour for the logic circuit. This allows ten minutes between the end of the power unit hour and the end of the logic system hour which allows for any margin of timing error in the power unit movement due to increased work load.

Mention has already been made of the prior employment of implanted circuitry having a simple programming capability for rate and amplitude control in a cardiac pacemaker type device as illustrated in U.S. Pat. No. 3,833,005. It has also been mentioned that such programmable circuitry has been shown to be controllable with an extracorporeal transmitter. However, such circuitry has not heretofore been employed in an implanted long term medication environment. In this regard, the present invention, in a further embodiment, employs a microprocessor and memory interfaced with or in place of the timed data evaluation and decision control circuitry, previously explained. Appropriate input and output circuits are employed to give the overall system a more general programmable capability which can be set to particular programs through use of an extracorporeal pulse transmitter or needle activated switch.

FIG. 20 is a general schematic representation of an extracorporeal program controller 350 used in conjunction with a programmable implanted medication device 351 as later described in more detail. In FIG. 21 program controller 350 is indicated as being an extracorporeal coding pulse transmitter akin to the coding pulse transmitter previously mentioned in connection with U.S. Pat. No. 3,833,005. With transmitter 350 there is employed an appropriate receiver circuit 355, a Control Memory Latch circuit means 356 as previously discussed in conjunction with FIG. 16 and a programmable circuitry which includes appropriate microprocessor and memory circuitry providing signal processing and via an analog to digital converter (353) interface appropriate logic interfaces for controlling timing, periodic sensing, evaluation and dispensing. This programmable circuitry provided by receiver 355, memory latch 356 and circuitry 357 is suitably connected to the appropriate sensor represented by sensor 358 in FIG. 21. To complete this system the controlled medication dispensing means 360 which may be of the bellows type previously explained is suitably connected to the medication storage 361 and with a suitable outlet 362 for transferring the dispensed medication to a catheter, or the like, to the treated site.

The general concept of providing programmable dispensing control circuitry and extracorporeal program controller means may of course be employed in conjunction with the previously described systems illustrated in FIGS. 1-6, 11, 12, 15 and 16. In order to illustrate one such application, there is schematically illustrated in FIG. 22 a system similar to the system of FIG. 11 with the addition of the program controller 350. In FIG. 22 the numerals for parts which are identical in FIG. 11 and FIG. 22 are duplicated and the dispensing means shown in detail in FIG. 11 has been generally indicated in FIG. 22 as being the "controlled medication dispensing means". Of particular interest to the present invention is the employment of a programmable circuitry 370 having the elements illustrated in FIG. 21 and which is subject to being controlled by the extracorporeal program controller 350 illustrated in FIG. 22. Thus, by the employment of appropriate coding pulses in the invention embodiment of FIGS. 20-22, the conditions under which medication is dispensed can be immediately changed and without involving any physical entry to the body carrying the implanted housing 150.

A general description of the programmable character of the invention having been given, the description next turns to a more detailed description of a representative programmable circuitry based on employment of the current model Fairchild F-8 type microprocessor series and using legends and terminology appropriate to such circuitry as understood by those skilled in the art and which is particularly illustrated in FIGS. 23-26. Representative descriptions of the F-8 series can be found in: "Fairchild Readies Bipolar Processors", Electronics, Feb. 20, 1975 and F-8 Microprocessor Catalog (1975), Semiconductors Components Group, Fairchild Camera and Instrument Corporation, 464 Ellis Street, Mountain View, Calif. 94042. While those skilled in the art will immediately appreciate the wide range of applications offered by the programmable character of the invention, the description will use as an example the employment of the invention for prevention of recurrent tachycardias which has been previously explained in connection with FIGS. 12, 13 and 16-19.

Since FIGS. 23-26 are basically self-explanatory to those skilled in the art, the explanation to follow will be primarily directed to aspects of the invention that might not be readily apparent. In this regard, it should be noted that the digital electronics inherent in the method and system of FIG. 16 can either be replaced by the microprocessor system as illustrated in FIG. 23 or the entire discrete electronic component control system can be replaced with a microprocessor based system as illustrated in FIG. 24.

Referring back to the description already given with reference to FIG. 16 and bearing in mind that FIG. 23 uses the schematic diagramming, terminology and legends appropriate to a Fairchild F-8 microprocessor-type system, it can be seen that the circuitry of FIG. 23 even though offering a wide ranging programming capability for internal medication dispensation operates basically like the previously explained circuitry of FIG. 16. For example, it can be seen that the system of FIG. 23 provides a microprocessor program, stored in one or more program storage units (3851-PSU), that follows the logic flow of FIG. 16 and results in the operation of the pump control and pump in exactly the same manner but with a far greater range of possible pump control operations. The inputs to the microprocessor system as illustrated in FIG. 23 are from the FIG. 16 QRS-detector and Memory Latch Controls 1 and 2, through appropriate input/output (I/O) ports as seen in FIG. 23.

As previously mentioned, the entire discrete electronic component control system shown in FIG. 16 can be replaced with a microprocessor system receiving cardiac electrical information through an Analog-to-Digital Converter (ADC), as well as transmitting and receiving information from external devices through an "External Interface" as shown in FIG. 24.

In the embodiment illustrated in FIG. 24, the ADC digitizes the analog QRS signal and transmits this information to the microprocessor for QRS-complex recognition and program evaluation. QRS-complex recognition is accomplished by using the same logic flow as in FIG. 16 and according to a later described flow chart. Thus, in this embodiment the QRS-complex recognition is accomplished by a program subroutine within the microprocessor system.

The External Interface seen in FIG. 24 can supply information through Memory Latch Controls as previously explained, thus enabling the microprocessor component of FIG. 24 to operate similarly to the electronic control system of FIG. 16. However, it will be seen that the type of microprocessor system illustrated in FIG. 24 is much more versatile than the electronic component system of FIG. 16 because of its facile reprogrammable feature as well as its simple but versatile peripheral interface structure. It should be appreciated that the mentioned "External Interface" seen in FIG. 24 can receive or send information using many different peripheral devices, such as memory latch controls, switches, R-F transmitters, receivers and the like. The External Interface thus enables information to be sent to and from the microprocessor in the form of programming changes and/or program operation constraints. Likewise, information processed by the microprocessor system can be transmitted to peripheral devices.

Communication with external sources can be accomplished quite easily with the method and microprocessor medication system of the invention. One means of communication with the implanted microprocessor medication control system is through the needle-rotary switch connector previously explained in connection with FIGS. 16 and 18–19. As further illustrated in FIG. 25, information can be sent to the implanted microprocessor medication control system with a keyboard that is connected via the needle switch to the microprocessor I/O ports, as illustrated in FIG. 25. Such information can, for example, be in the form of medication program changes, or program operation constraints. Similarly, by connecting a display screen or line-printer via the needle switch to the microprocessor I/O ports as further illustrated in FIG. 25, a readout of program operation parameters, the medication program itself, or of any memory buffers, can be obtained. Readout of the signal analysis buffers can, in many situations, provide the physician with valuable clinical information.

As previously mentioned in connection with FIGS. 20–22, another means of communicating with the microprocessor system is through an R-F transmitter-receiver pulse control system which may be of the type found in U.S. Pat. No. 3,833,005 and as further illustrated in more detail in FIG. 26. The transmitter and code generator, located externally to the body, as seen in FIG. 26, is a device available to the physician to send information to the receiver connected to the microprocessor unit. The receiver and decoder network shown in FIG. 26 receives the information sent by the transmitter and converts this information into usable input signals sent to the I/O ports of the CPU component indicated in FIGS. 23 and 24. Information transmitted to the microprocessor unit in the system and method of the invention is envisioned as being basically of two types; namely, program information and operation information. Program information is that which changes, modifies, or adds to the medication program of the microprocessor unit. For example, the modification of a subroutine can be accomplished by sending the coding for the changes to the microprocessor unit. Operation information is that which supplies the constraints necessary for the operation of the medication program. For example, the weights necessary for time period classification can be sent to the microprocessor unit for a particular medical situation.

The means of information processing in the transmitter-receiver network of the type illustrated in FIG. 26 is coded similarly to the system described in U.S. Pat. No. 3,833,005. Each of the two types of information mentioned may have its own code and subcodes within each structure. This coding procedure assures that the medication control information whatever it might be is channeled to its designated destination in the proper sequence.

Access to the I/O ports of the microprocessor unit via the transmitter-receiver network illustrated in FIG. 26 should be made possible only through the transmitter of the proper access-sequence code "keyed in" through the code generator on the transmitter. This access-sequence code can thus be restricted and made available only to the physician.

According to the method and system of the invention illustrated in FIG. 26, information transmitted to the implanted receiver-decoder shown in FIG. 26 will be simultaneously monitored by an external receiver seen in FIG. 26 so that the information being transmitted can be directly read out. This procedure allows the physician to check that the information transmitted is exactly the program requirements. It is recognized that this means of changing the evaluation programming does not allow for checking the implanted device coding; thus, any major revision or revision with potential serious consequences is intended to be accomplished by the more positive needle-switch system described previously, which allows for direct readout of the microprocessor memory through the same input/output ports through which it was read in. In addition, the needle-switch system allows monitoring of the evaluation program while in operation. Thus, there are several different means of insuring absolute accuracy of the operating system.

Use of a small, hand-held transmitter capable of being carried in one's clothes pocket can be employed and provides a means of allowing the patient specific limited access to the receiver-decoder network as is necessary. That is, the code generator-RF transmitter seen in FIG. 26 may in some cases represent a patient operated device and in other cases a physician only operated device. Such small matchbox-size transmitters are known and in required cases may be used with the invention circuitry to allow the patient limited options for changing specific operations. As an example one use which is anticipated is that of enabling the patient to activate a pump mechanism on demand via the microprocessing unit for a single dose, but under limitations provided by the program; that is, under specific requirements that would prevent two or more doses of the medication being given except under time constraints in the system program. Such a use for example can be provided in the special case where a second pump is available as illustrated in FIGS. 6, 8, 9 and 11, whereby the patient can activate a dose of a vasodilating medication directly through the pericardial sac when needed in cases of cardiac insufficiency.

A unique advantage of the microprocessor system and method embodied in FIG. 24 is that the system can be programmed using basically the same logic flow as described in FIG. 16 and which readily adapts to changing medication needs for particular patients or patient conditions. An outline of a program for operating the microprocessor in this manner can be flow-charted as follows: in what is hereafter referred to as the "Main Flow Chart".

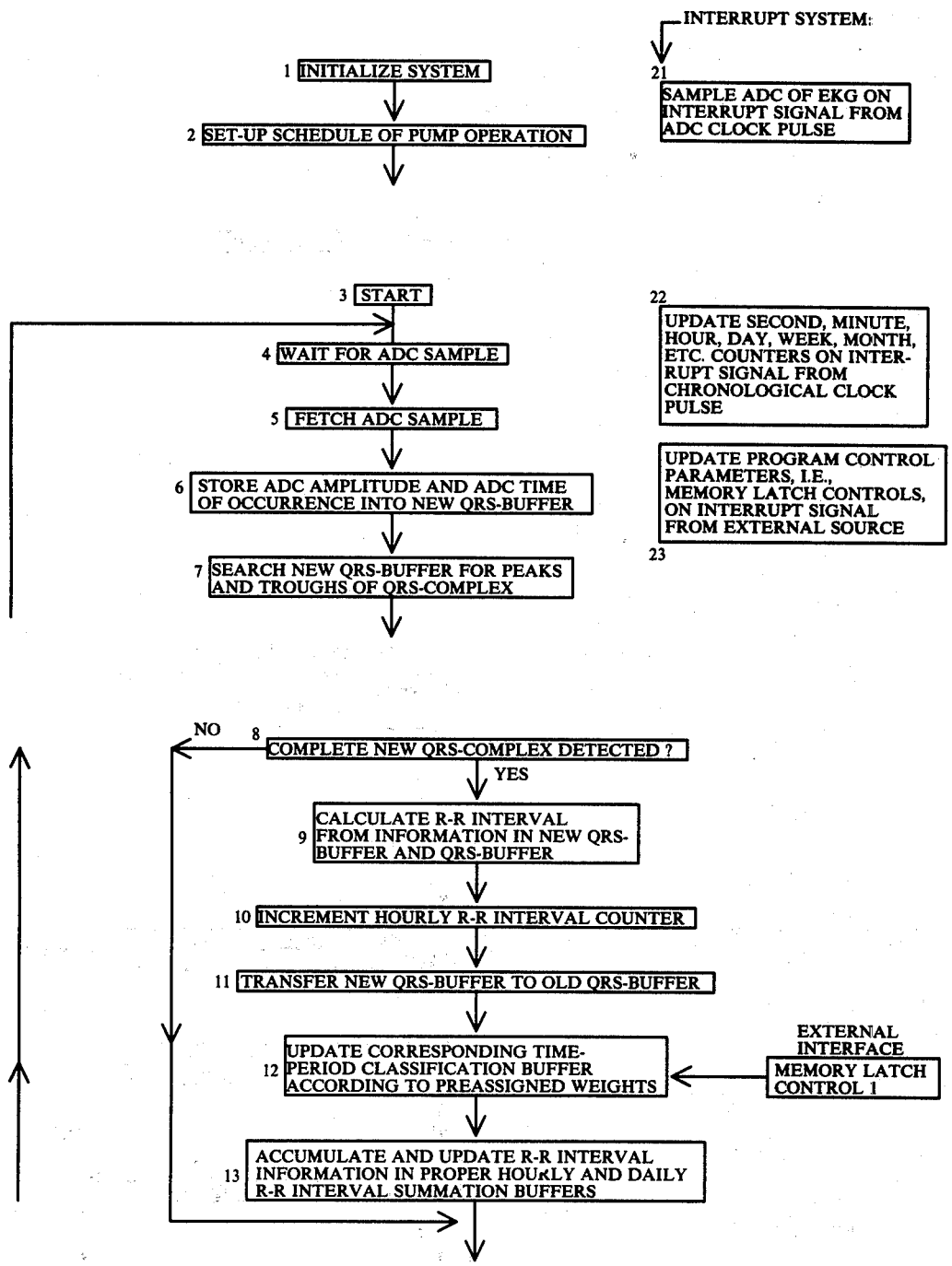

-continued
MAIN FLOW CHART
Microprocessor Program To Operate Pump Based On Incoming EKG ADC Information

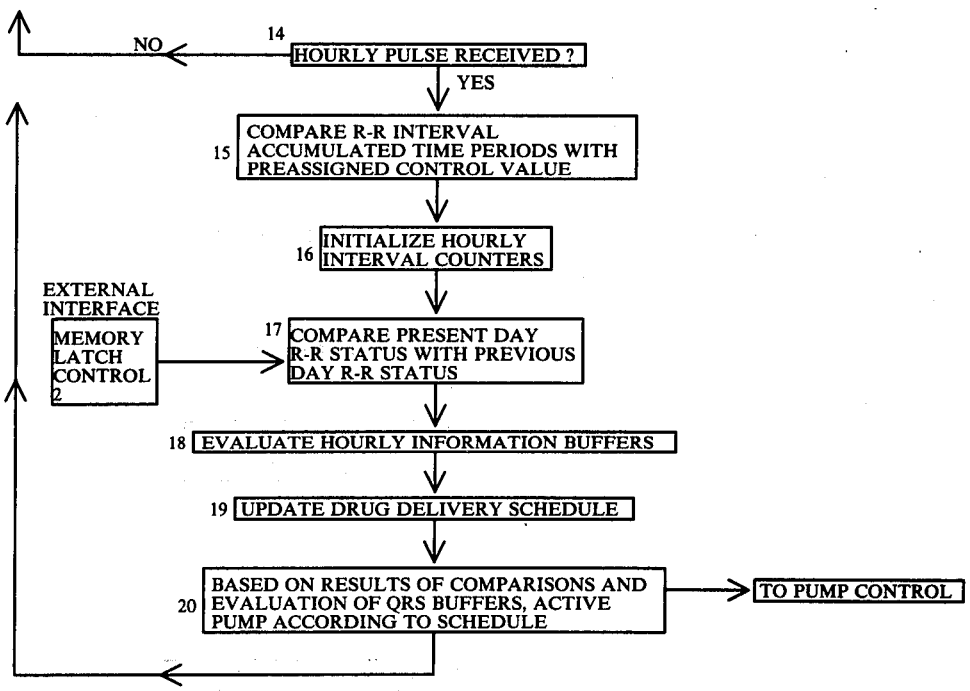

To exemplify the program structure of the individual blocks, or subroutines, in the foregoing chart, a few subroutines will next be shown in detail. These subroutines, as well as any and all subroutines within the program, can easily be changed by entering the proper coding changes into the microprocessor Program Storage Unit (PSU) through the I/O ports by the methods of communication previously described. The selected subroutines are as follows:

PUMP OPERATION SET-UP SUBROUTINE
Subroutine To Set-Up Schedule Of Pump Operation
(Block 2 Of Main Flow Chart)

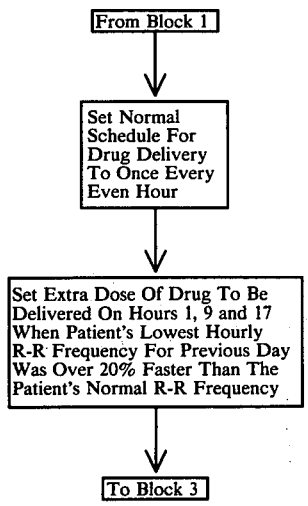

UPDATE TIME PERIOD SUBROUTINE
Subroutine To Update Corresponding Time-Period Classification Buffer According To Preassigned Weights
(Block 12 Of Main Flow Chart)

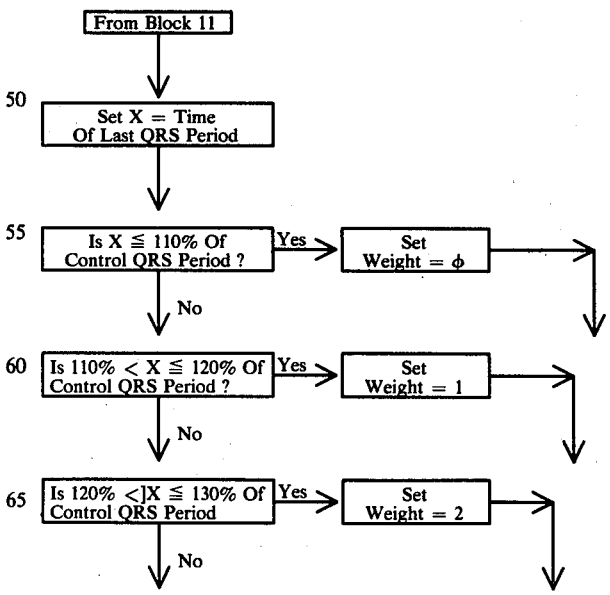

UPDATE TIME PERIOD SUBROUTINE
Subroutine To Update Corresponding Time-Period Classification Buffer According To Preassigned Weights
(Block 12 Of Main Flow Chart)

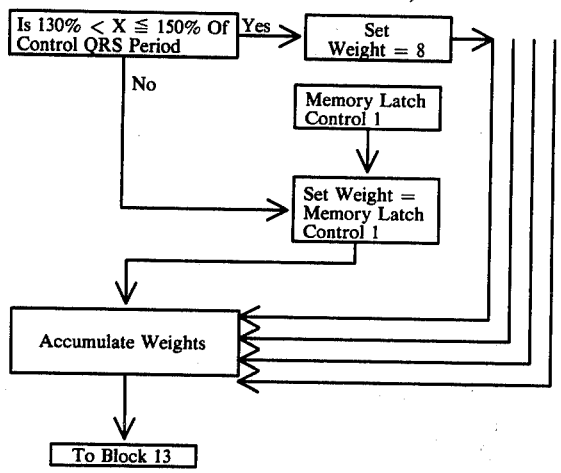

UPDATE DRUG SCHEDULE SUBROUTINE
Subroutine To Update Drug Delivery Schedule
(Block 19 Of Main Flow Chart)

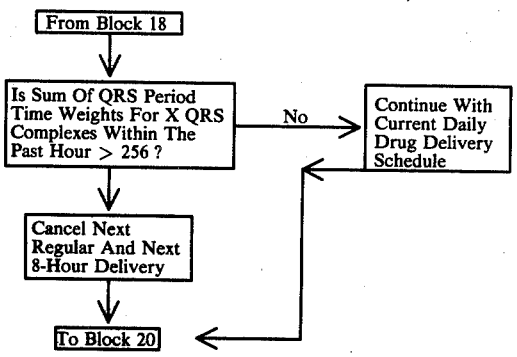

If a program change is desired to alter the logic flow of the program previously outlined, then the subroutines involved with this change can be modified. Useful information concerning QRS complex detection can be found in the reference: "Analogue Preprocessor For The Measurement By A Digital Computer Of R-R Intervals And R Wave Widths" — A. Sandman, D. W. Hill, A. H. Wilcock, Medical And Biological Engineering, March, 1973. In some cases new subroutines may be added and/or old subroutines may be deleted. For example, several program changes are possible if the pump and pump control mechanism is initially structured to deliver a potential dose three times each hour. Timer control of drug delivery can be programmed for example using the following constraints:

Program Change 1: Change conditions I of FIG. 17 such that the pump dispenses two doses each hour for normal operation.

Program Change 2: Change condition II of FIG. 17 such that an extra dose of drug is dispensed every third hour when the patient's lowest average hourly R-R frequency for the previous day was over 20% faster than the patient's normal R-R frequency.

Program Change 3: Change conditions III of FIG. 17 such that the schedule of pump operation is as follows:

| Reduction Of Scheduled Drug Deliveries For Next Hour | Sun Of Weights, As Obtained By Metod Previously Outlined |
| --- | --- |
| No reduction | Sum ≦ 64 |
| Elimination extra every 3 hour dose if present | 64 < Sum ≦ 128 |
| Reduction of the 2 normally scheduled doses to 1 dose and elimination of extra every 3rd hour dose if present | 128 < Sum ≦ 256 |
| Eliminate all doses | Sum > 256 |

The above described program changes 1 and 2 may be accomplished by changing the subroutine previously identified as "Pump Operation Set-Up Subroutine" to the following subroutine:

SUPPLEMENTAL PUMP OPERATION SET-UP SUBROUTINE
Subroutine To Set-Up Schedule Of Pump Operation
(Block 2 of Main Flow Chart)

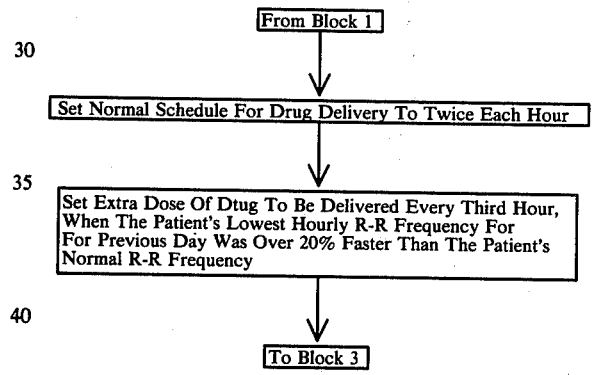

In a similar sense the previously identified program change 3 may be accomplished by changing the subroutine previously identified as "Update Drug Schedule Subroutine" to the following subroutine:

SUPPLEMENTAL UPDATE DRUG SCHEDULE SUBROUTINE
Subroutine To Update Drug Delivery Schedule
(Block 19 Of Main Flow Chart)

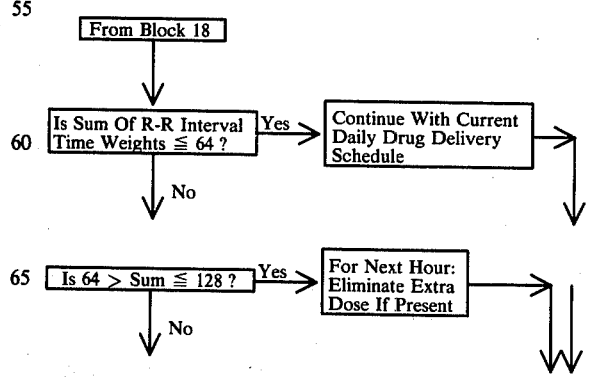

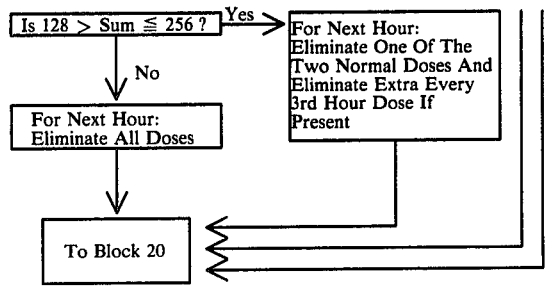

-continued
SUPPLEMENTAL UPDATE DRUG SCHEDULE
SUBROUTINE
Subroutine To Update Drug Delivery Schedule
(Block 19 Of Main Flow Chart)

In another aspect of the invention it is recognized that many cardiac cases would be benefited by having available both a pacemaking source as well as a medication source. Thus, the invention contemplates a method and system associated with an implanted structure utilizing a common control having at least some adjustable parameters and associated with both a pacemaking mechanism and a medication dispensing mechanism. The description has already dealt with sensing heart activity and treatment by medication related to such activity. Mention has also been made in connection with FIG. 18 of employing cardiac stimulation in conjunction with controlled medication as related to an implanted system and method using such a system. Thus, it is believed those skilled in the art will readily appreciate and understand the concept of combining both pacemaking and medicating functions in a unitary implanted system.

FIG. 27 broadly illustrates an implanted system having both pacemaking and medicating capabilities according to the invention. FIG. 28 illustrates in more detail a similar system utilizing both the medical and circuitry technology previously described. In order to more fully understand the role of the pacemaking activity in conjunction with the medicating activity, a brief description will be given of certain aspects of pacemaking of particular interest to the invention. From the following description, the reader will gain a better appreciation of the value of an implantable cardiac pacer and medication dispensing combination with mutually shared components such as those involved with timing, sensing, cardiac evaluation and the power source.

Implanted, as well as non-implanted, cardiac pacer systems are well known to those familiar with the art. They are usually categorized as "competing" or "non-competing" according to their relation to heart activity and stimulus pulses. There are two types of non-competing pacer systems of particular interest to the present invention and in which the stimulating pulses are synchronized with the R-R wave if there is one and which rely on recognition of cardiac waves by means of implanted electronic circuitry. The non-competing pacer is usually referred to as either a synchronous pacer or as a demand or stand-by pacer. Those familiar with the art readily understand the nature and distinction of these two types. Examples may be found in U.S. Pat. Nos. 3,528,428; 3,662,759; 3,677,251; and 3,911,929.

My prior U.S. Pat. No. 3,692,027 discloses self-powered, predetermined self-timing medication dispensing and my copending Application Ser. No. 463,262, now U.S. Pat. No. 3,923,060, discloses apparatus and methods for dispensing medications on the basis of body needs. This invention associates pacemaking with both types of systems. The description already given further demonstrates a method using the evaluation of the cardiac "QRS complex" and R-R interval parameters for sensitive dispensing of drugs for the treatment of cardiac arrhythmia based on the need of the body for this medication. The relation of cardiac pacemaking to cardiac medication thus becomes apparent. The method previously described also evaluates the potential cardiac toxicity of such drugs by assessment of the cardiac electrical signals in order to prevent toxic overdoses. Such a method thus allows for the dispensing of potent drugs directly through the pericardial sac, a method that could lead to potential hazards without the evaluation methodology of the present invention. The medication method of the invention thus allows for the complete cessation of medication dispensing when not needed and allows for the immediate resumption of dispensation when acute events occur within the heart, for example, myocardial infarction; thus allowing a sensitive monotoring system adapted to provide for treatment in emergency situations prior to the time the patient can be hospitalized and treated.

In the treatment of cardiac tachycardias, overdrive pacing is usually a temporary treatment for the critical period until the irritability is diminished by the beneficial effects of pacing or until the transient factors causing the irritability are no longer present. Included in these transient factors are digitalis intoxication, electrolyte imbalances, arrhythmogenic effects of cardiac surgery, myocarditis, or acute myocardial infarction. There are, however, instances in which long-term overdrive pacing from either the atrium or the ventricle may be necessary (Desanctis, R. W. and Babb, J. D.: The Role Of Pacing In The Management Of Cardiac Tachyarrhythmias in Cardiac Pacing by Philip Sammet, Grunne & Stratton, N.Y. & London, 1973, pp. 223-240).

Also to be considered is the fact that drugs used in the suppression of cardiac arrhythmias, such as quinidine, procainamide, diphenylhydantoin, and especially propranolol, may also depress the activity of the sinus node further slowing the heat rate and indeed inducing ventricular irritability. By allowing the pacer to control the heart rate, the use of these drugs allows for considerably more vigorous treatment, thus the combination of pacing and antiarrhythmic agents can be therapeutic where singly they were ineffective. In the treatment of recurrent tachycardias, a conservative approach to the use of pacing is appropriate unless symptoms of bradycardia are also present.

A variety of pacemaker options are available, including the "bifocal demand pacemaker" introduced by Berkovitz, Castellanos and Lemburg (Berkovitz, B. V.; Castellanos, A. and Lemburg, L.: Bifocal Demand Pacing in Circulation, Vol. 13, Suppl. III, p. 44, 1969, Abstract). This unit is primarily a sequential AV pacemaker that functions on demand. A ventricular electrode senses the ventricular electrical wave and sequentially paces the atrium and ventrical on demand. With this device, if the atrium is not stimulated, or in the presence of atrial tachyarrhythmias, or complete heart block, the pacemaker functions simply as a standby ventricular demand unit. Several techniques have been used for intermittent stimulation of the atria and ventricles for interrupting reciprocating tachycardias, including: (1) demand pacemakers, capable of switching to non-demand fixed rate modes by an external magnet; (2) inactive pacemaker units switched on by the magnet.

Thus, there are a variety of cardiac pacemakers that would be appropriate in selective cases for cardiac rhythm evaluation controlled pacemaker and drug-dispensing combination units. In general, when ventricular pacing is used to control arrhythmias, especially in overdrive pacing, demand pacing is chosen to diminish the incidence of ventricular irritability induced by pacing. Thus, the cardiac pacemaker requires evaluation of the ongoing QRS wave or P-wave to determine proper pulsing.

Turning more specifically to the prevention of recurrent tachycardias, both supraventricular and ventricular tachycardias have more recently been indications for the use of pacemakers because: (1) the normal rate can be induced in cases of bradycardia where it alternates with paroxysmal tachycardia; (2) pacing may increase the threshold for ectopic discharges and even ventricular fibrillation (Schoenfeld, C. D. and Bhardwaj, P.: Indications For Cardiac Pacemakers in Cardiac Pacing by Philip Sammet, Grunne & Stratton, N. Y. & London, 1973, pp. 143–167).

Supraventricular tachycardias, especially those secondary to sinus bradycardia, have good results when treated with a combination of drugs and demand pacemaking. Ventricular tachycardias are also an indication for the use of pacing as mentioned earlier. Possible indications for use of permanent pacing for recurrent ventricular arrhythmias include: (1) failure of drug therapy to control ventricular tachyarrhythmia; (2) patients requiring toxic doses of antiarrhythmic drugs to control the ventricular arrhythmia; (3) patients developing sinus bradycardia or a.v. block in response to drug treatment for the ventricular arrhythmias; (4) ventricular irritability in response to needed digitalis treatment; (5) patients with adverse reactions to anti-arrhythmic drugs. Most often patients require a combination of pacing and drug treatment to control the arrhythmias, and indeed some cardiologists use permanent atrial or ventricular demand pacing in most of their recurrent drug-resistant ventricular arrhythmias (see Schoenfeld and Bhardwaj reference previously cited).

Thus, in summary, use of combination cardiac pacemaking and drug treatment of the arrhythmias, e.g., ventricular arryhthmias is a unique specific therapy. The ventricular tachycardia, when recurrent is usually paced with a demand pacemaker with combined drug treatment including quinidine. Prior description has dealt with a method for selective antiarrhythmic medication dispensing, or specifically quinidine, in the treatment of the supraventricular tachycardia. This medication, based on the evaluation of the cardiac rate and potential toxic effects indicated by electrophysiological changes, provides for a sensitive administration of drugs such as quinidine. In the herein disclosed combination dispenser-pacer apparatus which can be used for the treatment of recurrent supraventricular tachycardia, quinidine can be dispensed according to the contingencies previously described, thus carefully avoiding toxic levels. However, the possibility of inducing a bradycardia which occurs even at non-toxic doses, must be considered. In this case, the demand pacemaker can continue to pace the heart at an adequate rate thereby reducing the possibility of increasing ventricular irritability secondary to the bradycardia. Furthermore, the pacemaker can be converted to a fixed rate mode by the previously described needle operated switch operator or by the usual means of a magnet switch. Thus, the combination of an evaluator-controlled pump and pacemaker provide a series of safety options that sequentially come into operation under various cardiac conditions, in addition to providing a combination that is frequently mentioned in the literature as being the most effective treatment, that is, combined drug and pacing for certain cardiac arrhythmias.

Certain details are important in the consideration of programming the medication dispensing with the combined pacemaker. Obviously, the cardiac waveform elicited by the demand pacemaker should not be counted in the QRS period or R-R interval evaluations; thus, any pulse produced by the pacer should be programmed to block the induced cardiac electrical change from consideration of the evaluator circuitry thus insuring that a widened QRS produced by a pacemaker pulse will not be considered for evaluation of quinidine toxicity. Other considerations concerning the interaction of the dispenser-evaluator system and the cardiac pacing manifestations will also have to be considered, both on an individual basis and in the more general case. However, the flexible programming system described allows for a versatile adjustment of the evaluator system to take many possibilities and outcomes into consideration. More specifically, the microprocessor flexible programming will allow for individual consideration of a patient's need for specific drug dispensation and cardiac pacing.

The combination pacer-dispenser provides for one additional important treatment that is an example of flexibility of the apparatus. The ventricular tachycardia can be adequately sensed-evaluated by the system described in my U.S. Pat. No. 3,923,060, but the widened QRS complex indicating the slow conduction in quinidine toxicity is not as specific, since the QRS in ventricular tachycardia often has a long period itself. The pacer combination allows for pacer stimulation at a point upstream from sensing electrodes thus providing a means of monitoring the conduction time or estimating the QRS period. Since quinidine produces an increasing prolongation of the conduction velocity as toxicity develops, measurement of the conduction time provides a measure indicating toxicity. Thus, the combination allows a specific evaluator-based treatment for ventricular tachycardia that would have been difficult to program without the pacer stimulus pulse control. A useful reference in this regard and which is concerned with the subject of detecting the QRS complex and computing the R-R interval is found in "A QRS Preprocessor Based on Digital Differentiation" by William P. Holsinger, Kenneth M. Kempner and Martin H. Miller, IEEE Transactions on Bio-Medical Engineering, Vol. BME-18, No. 3, May 1971, pp. 212–217.

As further background for illustrating both the need for and the practicality of combining heart pacing and medication dispensing in a unitary system, it may be noted here that U.S. Pat. No. 2,690,178 illustrates non-implanted prior art apparatus for the dispensing of drugs in response to body generated signals. British Pat. No. 769,876 describes another non-implanted system for dispensing drugs in response to electrically induced muscle activity. U.S. Pat. No. 3,651,806 represents another non-implanted device in which drugs are dispensed in response to signals transmitted to and from the heart. U.S. Pat. No. 3,701,345 also relates broadly to a non-implanted system in which fluid dispensing is synchronized with heart cycles.

FIG. 27 demonstrates broadly and FIG. 28 in more detail the common elements of the combination pacer and dispensing device that can be shared. These include the cardiac electrode sensor, external to the housing, the cardiac signal amplifier, the analog-to-digital interface to the microprocessor or other suitable logic and timing circuitry, the micropower source, the input/output portal, and the external interface. Either a common or independent housing (with appropriate connections) is envisioned. Also illustrated in FIG. 28 are the separate components needed for the dispensing device as well as the pacemaker. Use of the analog-to-digital circuitry and microprocessor allows for similar programs to have dual purposes. For example, the QRS detector and QRS period analyzer, the R-R period analyzer and other evaluations can be jointly used for decision-making about cardiac medication dispensing as well as for timing and control decision for the demand pacemaker. Such a use provides an economical package which adds the demand pacemaker to the programmable medication dispensing device with only the addition of the pacemaker control circuitry and pulse stimulator.

In interpreting FIGS. 27 and 28, it should, of course, be understood that any of the medication dispensing components or circuit components such as illustrated in FIGS. 1 through 26 of the present application or as illustrated in my prior U.S. Pat. No. 3,692,027 could be employed in the configurations of FIGS. 27 and 28. Other controllable medication dispensing arrangements that could be used in conjunction with cardiac pacemaking will become apparent to those skilled in the art. It will also be recognized that by using buffer storage, the readout and programming system previously described in the "Main Flow Chart" and "Subroutine" and in connection with FIGS. 16 and 18 and FIGS. 23 through 26, an accommodation to changing patient needs becomes both realistic and adaptable to highly complex situations.

At this stage of development it is contemplated that most applications of the invention will be best met by use of an integrated system having a single housing for containing the medication storage, the power source, the dispensing means and the programmable control. Also, where heart pacing is coordinated with medication it is contemplated that most applications would be best served by housing the pacemaking control in the same housing as the medication control. However, as illustrated in U.S. Pat. No. 3,527,220, in my own prior U.S. Pat. No. 3,692,027, and in U.S. Pat. No. 3,919,722, and while not shown in the present application, it is recognized that a totally implanted system and particularly an integrated programmable medicating system as represented in this invention, with or without coordinated pacing functions, does not inherently require the employment of a single housing.

The present invention thus contemplates that the implanted housing means might be a unitary housing or, in some instances, plural housings. For example, the medication storage could be housed separately as in one example in my prior U.S. Pat. No. 3,692,027 or the medication control with or without pacing control could be housed separately and still utilize a common implanted programmable control as part of an overall integrated system. Also, the dispensing means and medication storage means could comprise a separately housed electrically controlled unit and the form of medication storage could be adapted to the particular kind of medication being dispensed. Such an arrangement of separately housed components could employ, for example, an electrode controlled drug dispensing mechanism using iontophoretic methodology. See for example: "Drug Pacemakers in the Treatment of Heart Block" by Judah Folkman and David M. Long, Jr., Annals of the New York Academy of Sciences, V. III, Art. 1-3, 1963-64, pp. 857-868.

In summary, there has been described an implantable system and method specifically useful for treating the human and animal body in a unique way. The "power source" may take many forms. It may be in the micropower form referred to in my prior U.S. Pat. No. 3,692,027 or in other equivalent miniaturized forms providing a long life, i.e., measured at least in terms of days and preferably years, source of electrical energy, for energizing the system electronics and for providing power for the drive member used to actuate the dispensing mechanism. The apparatus lends itself to a wide variety of applications and the medication may include pharmacologically active drugs needed, body constituents, energy compounds, radioactive materials, and the like.

It should also be noted that the term "body" and "animal body" as used in the claims are intended to include animal, human and other living bodies. Further, the term "body" is intended to encompass any environmental body, whether living or otherwise adapted to receiving a self, micro-powered and timed device for incremental dispensing of substances into such body.

Of particular importance to the present invention is the employment of dispensing control circuitry which can be modified through means external of the implanted system to change the "program", i.e., the electrical response character of the control circuitry to input information received in electrical form. With such reprogrammable capability, there is now provided an implantable system and method of medication with or without pacemaking and having a substantially large number of variables which can be programmed to match both the immediate and changing conditions of a wide range of patient needs. For simple selectivity, e.g., a choice of two programs, the control operator could operate through a transduced magnetic or pressure coupling and the "signal control" would thus be a transduced magnetic or pressure signal. Overall, the invention system is thus highly versatile.

What is claimed is:

1. A self-powered programmable apparatus adapted to be totally received within a selected animal body, including human, for periodically dispensing selected medication therein according to a selected program coordinated with need while leaving the body ambulatory at all times, comprising:

(a) a storage member mounted within the body for storing selected medication to be dispensed therein;

(b) a micro size power source mounted within implanted housing means and having a useful working life in terms of at least several days;

(c) miniaturized dispensing means mounted within implanted housing means and adapted to be operated under programmed electrical control to cause selected said medication to be discharged from the implanted storage member into said body; and (d) miniaturized programmable electrical control circuit means mounted within implanted housing means and connected to be energized by said power source, said electrical control means being adapted for performing control operations according to program instructions for actuation of said dispensing means, said control means embodying selectable and resettable plural program configurations, each program configuration providing a selection of logic stored digital control data corresponding to a set of predetermined body conditions and medical dispensation therefor, thereby providing in singular and plural programs associated therewith a complex programming capability accommodating differential times and rates, means for extracting said data and means for applying said data to operate said dispensing means, said circuit means being set in a configuration corresponding to one of such programs and being adapted to actuate said dispensing means according to the selected program to dispense said medication within said body at times and rates determined by said program.

2. An apparatus as claimed in claim 1 wherein said circuit means further includes pacemaking circuit means operationally associated and functionally coordinated therewith.

3. An apparatus as claimed in claim 1 including means incorporating said logic stored control data arranged for being reprogrammed to selectively alter corresponding logic operating instructions and thereby provide the capability for simple to complex reprogramming.

4. An apparatus as claimed in claim 3 wherein said circuit means further includes pacemaking circuit means operationally associated and functionally coordinated therewith.

5. An apparatus as claimed in claim 3 wherein said evaluation, timing and associated circuit means include and operate with memory means to store selected said data from said sensing means and said memory in conjunction with said timing means provide the capability for evaluating said sensed body condition data selectively in real or historical or abstract time.

6. An apparatus as claimed in claim 1 including:
(a) sensing means selectively placed within said body for producing sensed signals convertible to electrical data corresponding to a sensed condition within said body;
(b) connector means within said body and connected to said sensing means for transferring such signals to said circuit means to be processed therein; and
(c) within said circuit means data evaluation means connected through said connector means to said sensing means and adapted to receive selected data from said sensing means and convert such data into an electrically processable form and adapted for electrically evaluating such sensed data at selected times wherein actuation of said dispensing means is coordinated with evaluations of said data by said circuit means and as regulated by the selected said program.

7. An apparatus as claimed in claim 6 wherein said sensing means is operative both for said medication dispensing and pacemaking.

8. An apparatus as claimed in claim 1 including extracorporeal operator means operationally associated with said circuit means and operable extracorporeally to selectively select and set within said circuit means a particular configuration corresponding to a selected said program.

9. An apparatus as claimed in claim 8 wherein said circuit means includes means adapted to store selected said information in electrically retrievable form and said operator circuit means includes means to readout selected said information stored in said circuit means.

10. An apparatus as claimed in claim 8 wherein said operator means and circuit means are operatively associated through a rotary needle connector means adapted to electrically mate with and provide rotatable electrical hardwire connection with said circuit means for plural functions therein.

11. A self-powered programmable apparatus adapted to be totally received within a selected animal body, including human, for periodically evaluating selected internal physiological states of such body and for periodically dispensing selected medication substance therein according to such states while leaving the body ambulatory at all times, comprising:
(a) a storage member mounted within the body for storing selected substance to be dispensed therein;
(b) a micro size power source mounted within implanted means and having a useful working life in terms of at least several days;
(c) miniaturized implanted dispensing means connected to receive said substance from said storage member and adapted to be operated at selected times and being adapted when so operated to cause selected said substance to be discharged from the storage member into said body;
(d) sensing means selectively placed within said body for providing sensed signals convertible to electrical data corresponding to a sensed condition within said body;
(e) connector means connected to said sensing means for transferring such signals for processing;
(f) miniaturized electrical data evaluation and timing means mounted within implanted housing means and connected to be energized by said power source and comprising:
 (i) miniaturized electrical evaluation circuit means connected through said connector means to said sensing means and adapted to receive selected data from said sensing means and convert such data into an electrically processable form and adapted for electrically evaluating such sensed data;
 (ii) timing means operatively connected to said circuit means and providing both long term and short term electrical time base information thereto whereby said dispensing means is operated in coordination with selected evaluations; and
 (iii) associated circuit means responsive to external signal control enabling selected elements of said evaluation circuit and timing means to be selected and set in or to be reset to a selected operational program configuration selected from plural potential configurations therein, each program configuration providing a selection of logic stored digital control data accommodating for differential times and rates corresponding to a set of predetermined body conditions and needed substance dispensation therefor, thereby providing a complex programming capability determinative of the manner and mode of operation of said evaluation circuit and timing means; and
(g) control means located external of said body for producing said signal control to select said program or programs.

12. An apparatus as claimed in claim 11 wherein said evaluation, timing and associated circuit means include and operate with memory means to store selected said data from said sensing means and said memory in conjunction with said timing means provide the capability for evaluating said sensed body condition data selectively in real or historical or abstract time.

13. An apparatus as claimed in claim 11 wherein said associated circuit means includes switch contact means adapted to receive a needle connector for transmitting signal control through a hardwire connection and wherein said control means includes needle connector means enabling said signal control to pass therethrough to select a said program.

14. An apparatus as claimed in claim 1 wherein said storage member, dispensing means, sensing means and data evaluation and timing means are adapted for selectively dispensing plural sources of medication.

15. An apparatus as claimed in claim 11 wherein said storage member, sensing means, dispensing means and evaluation and timing means are adapted to storing, sensing the need for and dispensing doses of plural medications.

16. An apparatus as claimed in claim 15 wherein said dispensing means is adapted to dispensing said doses of plural medications to separate sites within said body.

17. An apparatus as claimed in claim 15 wherein said dispensing is according to plural sensing schedules.

18. An apparatus as claimed in claim 1 wherein said sensing means is adapted to sense and develop electrical signals corresponding to plural medical factors and said data evaluation and timing means is adapted to electrically evaluate said factors and dispense said substance medication according to such evaluation.

19. In an apparatus as claimed in claim 1 wherein said storage member stores a single medication, said dispensing member comprises plural dispensing means connected to a common said storage member and said data and evaluation timing means is adapted to evaluate the need for and to separately operate each such dispensing means to cause said medication to be dispensed independently through one or the other of said dispensing means.

20. In an apparatus as in claim 1 wherein said storage member, sensing means, dispensing means, data evaluation and housing means are adapted to sense the need for and to dispense a first medication on a regular timed basis and a second medication on a special basis.

21. An apparatus as claimed in claim 11 wherein said storage member, sensing means, dispensing means and evaluation and timing means are adapted to dispensing medication in a wide range of combinations of single and plural doses, medications, sensed conditions, sites, and timing schedules.

22. An apparatus as claimed in claim 11 adapted to dispense medication for prevention of recurrent tachycardias and arrhythmias and wherein said sensing means comprises a cardiac-type sensor and said data evaluation and timing means includes an amplifying circuit connected to said sensing means, a first QRS detector circuit connected to said amplifier, a second QRS period analysis and control value comparison circuit connected to said first QRS detector circuit, an R-R interval analysis and control value comparison circuit connected to said first QRS detector circuit and said QRS period analysis circuit, an evaluating logic circuitry connected to said second QRS period analysis and said R-R interval analysis circuit, a timing circuit connected to time said second QRS period circuit, said R-R interval analysis circuit and said logic evaluation circuit and wherein said dispensing means is controlled by said logic evaluation circuit.

23. A self-powered programmable apparatus adapted to be totally received within a selected animal body, including human, for periodically evaluating selected internal physiological states of such body and for periodically dispensing selected medication substance therein according to such states while leaving the body ambulatory at all times, comprising:
(a) a storage member mounted within the body for storing selected substance to be dispensed therein;
(b) a micro size power source mounted within implanted means and having a useful working life in terms of at least several days;
(c) miniaturized dispensing means connected to receive said substance from said storage member and adapted to be operated at selected times and being adapted when so operated to cause selected said substance to be discharged from the storage member into said body;
(d) sensing means selectively placed within said body for providing sensed signals convertible to electrical data corresponding to a sensed condition within said body;
(e) connector means connected to said sensing means for transferring such signals for processing;
(f) miniaturized electrical data evaluation and timing means and connected to be energized by said power source and comprising:
  (i) miniaturized electrical evaluation circuit means connected through said connector means to said sensing means and adapted to receive selected data from said sensing means and convert such data into an electrically processable form and adapted for electrically evaluating such sensed data;
  (ii) timing means operatively connected to said circuit means and providing electrical time base information thereto whereby said dispensing means is operated in coordination with selected evaluations; and
  (iii) associated circuit means responsive to external signal control enabling selected elements of said evaluation circuit and timing means to be set in a selected operational program configuration selected from plural potential configurations therein, said associated circuit means including switch contact means adapted to receive a needle connector for transmitting signal control reprogramming data through a hardwire connection and wherein said control means includes needle connector means enabling said signal control to pass therethrough to reprogram; and
(g) control means located external of said body for producing said signal control to vary said program or programs.

24. The method for periodically evaluating selected internal physiological states of an animal body, including human, and for periodically dispensing selected medication substance therein according to such states while leaving the body ambulatory at all times, comprising:
(a) implanting a storage member within the body and storing therein a selected substance to be dispensed therefrom;
(b) implanting a micro size power source having a useful working life in terms of at least several days;

(c) implanting miniaturized dispensing means connected to receive said substance from said storage member and adapted to be operated at selected times to cause selected said substance to be discharged from the storage member into said body;
(d) implanting sensing means for providing sensed signals convertible to electrical data corresponding to a sensed condition within said body;
(e) implanting connector means connected to said sensing means for transferring such signals for processing;
(f) implanting miniaturized electrical data evaluation and timing means and connected to be energized by said power source and comprising:
  (i) miniaturized electrical evaluation circuit means connected through said connector means to said sensing means and adapted to receive selected data from said sensing means and convert such data into an electrically processable form and adapted for electrically evaluating such sensed data;
  (ii) timing means operatively connected to said circuit means and providing electrical time base information thereto whereby said dispensing means is operated in coordination with selected evaluations; and
  (iii) associated circuit means responsive to external signal control enabling selected elements of said evaluation circuit and timing means to be set in a selected operational program configuration selected from plural potential configurations therein, each program configuration providing a selection of logic stored digital control data corresponding to a set of predetermined body conditions and needed substance dispensation therefor, thereby providing a complex programming capability determinative of the manner and mode of operation of said evaluation circuit and timing means; and
(g) positioning control means external of said body for producing said signal control to select said program or programs; and
(h) allowing said sensing means to operate, to produce signals corresponding to physiological states within the said body and allowing said substance to be dispensed to a selected site within the body on a schedule and program as determined by said data evaluation and timing means over a long period of time and by the program signal control established by said control means.

25. A self-powered programmable dispensing apparatus adapted to be totally received within a selected animal body, including human, for altering a selected internal state of such body and for periodically dispensing selected substance therein while leaving the body ambulatory at all times, comprising:
(a) storage means received within the body for storing selected substance to be dispensed therein;
(b) a micro size power source received within the body and having a useful working life in terms of at least several hours;
(c) miniaturized dispensing means received within the body and communicating with said storage means and being adapted when operated to discharge said substance from the storage means into said body; and
(d) miniaturized electrical control means received within the body and connected to be energized by said power source and comprising:
  (i) miniaturized electrical circuit means adapted to be selectively set and reset to any of various operating modes for establishing a control program for operating said dispensing means, each of said operating modes providing a selection of logic stored digital control data corresponding to a set of predetermined body conditions and appropriate substance dispensation therefor, means for extracting said data and means for applying said data to operate said dispensing means thereby providing a complex program capability; and
  (ii) timing means operatively connected to said circuit means and providing electrical time base information thereto.

26. A self-powered combined medicating and cardiac pacer apparatus adapted to be totally received within a selected animal body, including human, for periodically dispensing selected medication therein and pacing the heart thereof through electrodes connected thereto while leaving the body ambulatory at all times, comprising:
(a) a storage member received within the body and adapted to store selected medication to be dispensed therein;
(b) a micro size power source mounted within implanted housing means and having a useful working life in terms of at least several days;
(c) miniaturized electrical control means adapted to both provide controlled electrical impulses on electrode means for heart pacing purposes and electrical control for the operation of dispensing means, selectable and resettable circuit means within said control means providing a selection of logic stored digital control data corresponding to a set of predetermined body conditions and medication dispensation therefor, thereby providing in singular and plural programs associated therewith a complex programming capability, means for extracting said data and means for applying said data to operate said dispensing means and pace said heart according to the program mode in which said program circuit means has been set;
(d) miniaturized dispensing means connected to said storage member and adapted to be operated by said control means to cause said medication to be discharged from the storage member into said body;
(e) electrode means adapted to be connected to the heart of said body and having a connection to said control means for receiving electrical impulses for evaluation to pace said heart in coordination with dispensing of said medication; and
(f) selectable and resettable circuit means within said control means providing a selection of logic stored digital control data corresponding to a set of predetermined body conditions and medication dispensation therefor, thereby providing in singular and plural programs associated therewith a complex programming capability, means for extracting said data and means for applying said data to operate said dispensing means and heart pacing means according to the program mode in which said program circuit means has been set.

27. A self-powered combined medication dispensing and electrically stimulating apparatus adapted to be totally received within a selected animal body, including human, for periodically dispensing selected substance therein and electrically stimulating a selected organ thereof through electrodes connected thereto while leaving the body ambulatory at all times, comprising:

(a) storage means received within the body for storing selected substance to be dispensed therein for treating said body;

(b) a micro size power source mounted within implanted housing means and having a useful working life in terms of at least several days;

(c) miniaturized electrical control means adapted to both provide controlled electrical impulses on electrode means for organ electrical stimulating purposes and electrical control for the operation of dispensing means;

(d) miniaturized dispensing means connected to said storage means and adapted to be operated by said control means to cause said substance to be discharged from storage means into said body;

(e) electrode means adapted to be connected to a selected organ of said body and having a connection to said control means for receiving electrical impulses to electrically stimulate said organ in coordination with dispensing of said substance; and (f) selectable and resettable program circuit means within said control means providing a selection of logic stored digital control data corresponding to a set of predetermined body conditions and substance dispensation therefor, thereby providing in singular and plural programs associated therewith a complex programming capability, means for extracting said data and means for applying said data to operate said dispensing means and stimulate said organ according to the program mode in which said program circuit means has been set.

* * * * *

UNITED STATES PATENT AND TRADEMARK OFFICE
CERTIFICATE OF CORRECTION

PATENT NO. : 4,146,029

DATED : March 27, 1979

INVENTOR(S) : Everett H. Ellinwood, Jr.

Page 1 of 4

It is certified that error appears in the above-identified patent and that said Letters Patent are hereby corrected as shown below:

Col. 9, line 12, "interiorof" should be --interior of--.

Col. 16, line 10, "occuring" should be --occurring--.

Col. 16, line 31, "R" should be --R-R--.

Col. 16, line 60, --.-- should be inserted after "one" before the parenthesis mark.

Col. 18, line 28, "by", first occurrence, should be --be--.

Cols. 21-24 should be deleted to insert the attached cols. 21-24 therefor.

Col. 28, line 21, "monotoring" should be --monitoring--.

Col. 29, line 34, ":" should be --;--.

Col. 32, line 13, "preferrably" should be --preferably--.

Col. 25, line 35, beneath first block below block captioned "From Block 18" insert --Yes--

Col. 26, line 4, "Metod" should read --Method--

Col. 26, line 36, "Dtug" should read --Drug--

UNITED STATES PATENT AND TRADEMARK OFFICE
CERTIFICATE OF CORRECTION

PATENT NO. : 4,146,029

DATED : March 27, 1979

INVENTOR(S) : Everett H. Ellinwood, Jr.

It is certified that error appears in the above-identified patent and that said Letters Patent are hereby corrected as shown below:

Col. 35, line 31, "substance" should be deleted.

Col. 35, line 32, insert --substance-- after the word "medication".

Signed and Sealed this

Twenty-first Day of August 1979

[SEAL]

Attest:

Attesting Officer

LUTRELLE F. PARKER
*Acting Commissioner of Patents and Trademarks*

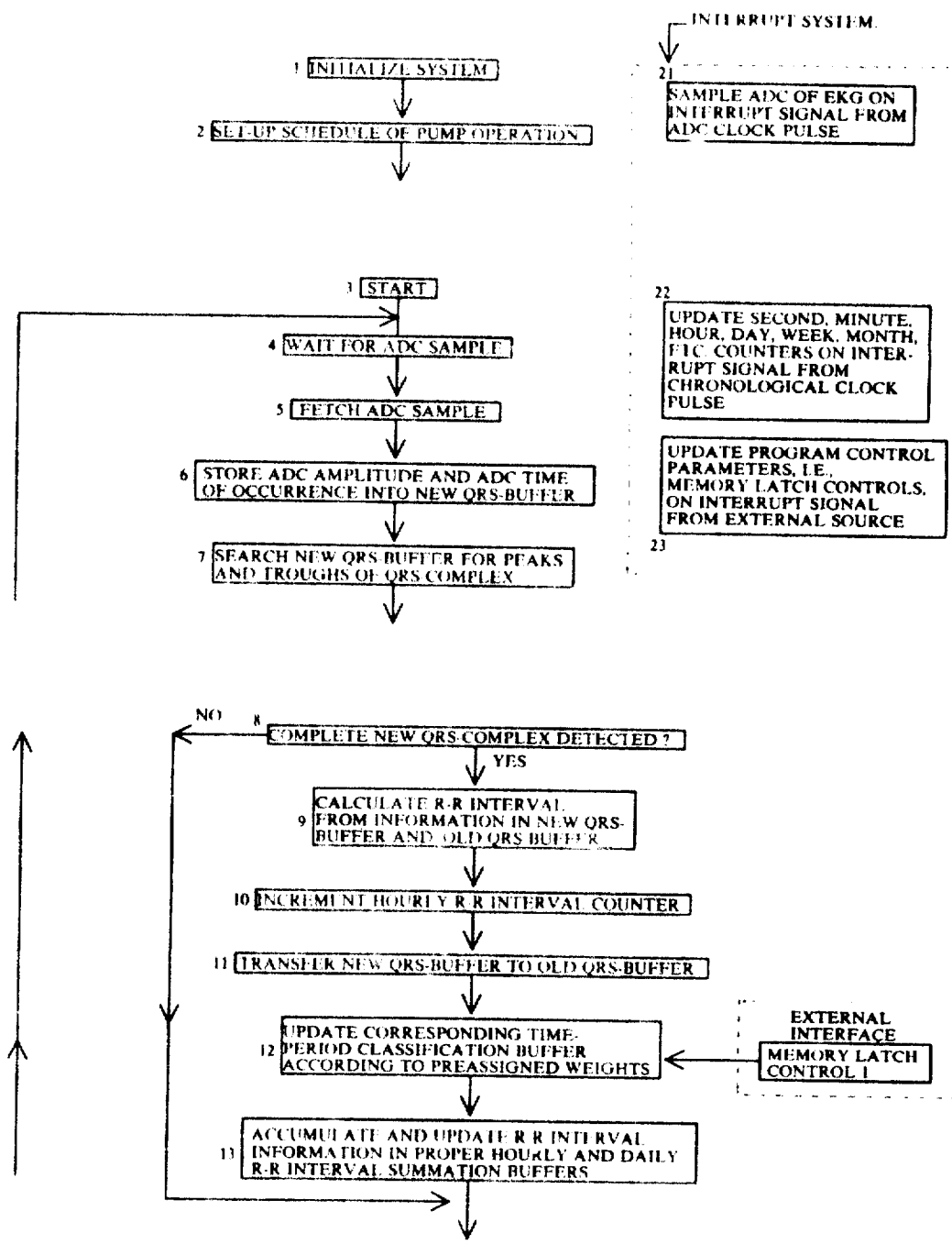

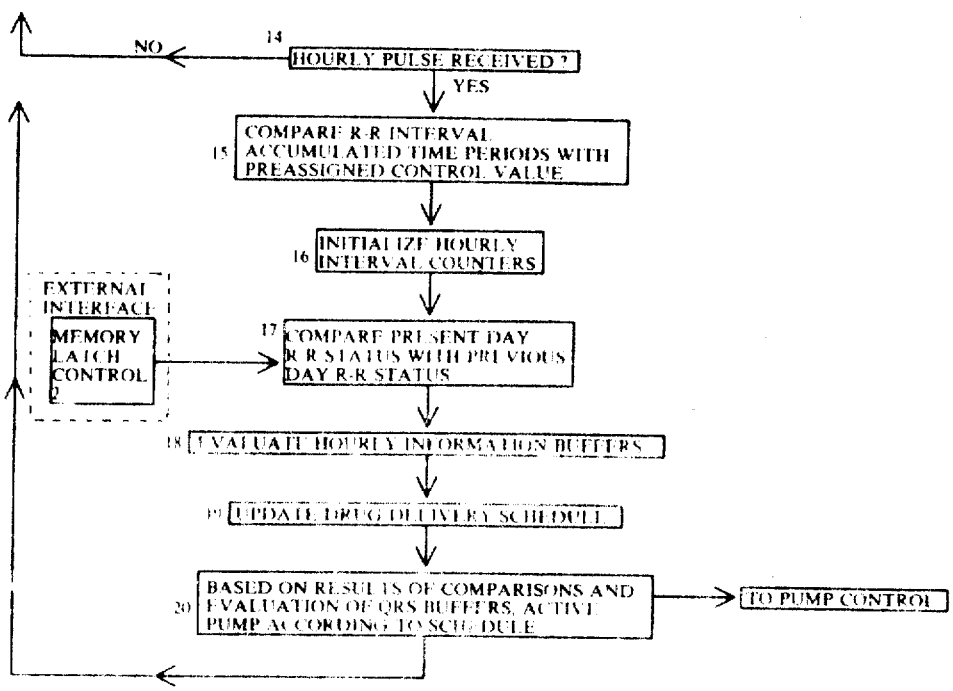

To exemplify the program structure of the individual blocks, or subroutines, in the foregoing chart, a few subroutines will next be shown in detail. These subroutines, as well as any and all subroutines within the program, can easily be changed by entering the proper coding changes into the microprocessor Program Storage Unit (PSU) through the I/O ports by the methods of communication previously described. The selected subroutines are as follows:

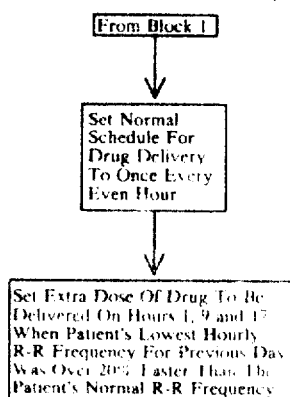

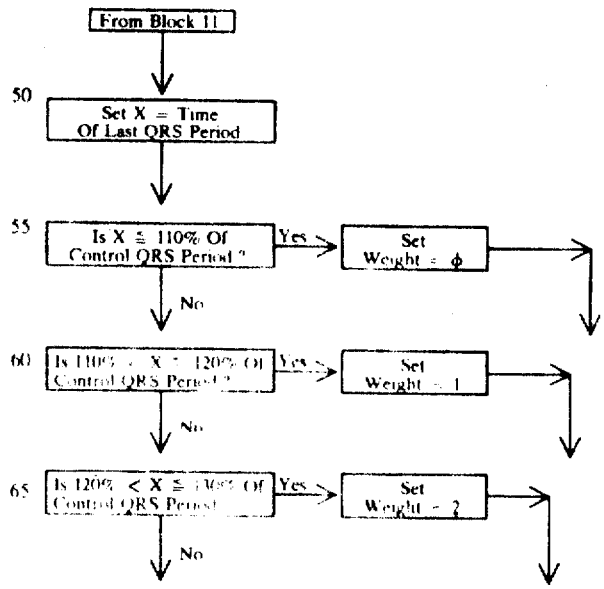

UNITED STATES PATENT AND TRADEMARK OFFICE

CERTIFICATE EXTENDING PATENT TERM
UNDER 35 U.S.C. 156

Patent No.    : 4,146,029

Dated         : March 27, 1979

Inventor(s)   : Everett H. Ellingwood, Jr.

Patent Owner  : Biomedical Systems Institute, Inc.

This is to certify that there has been presented to the

COMMISSIONER OF PATENTS AND TRADEMARKS an application under 35 U.S.C. 156 for an extension of the patent term. Since it appears that the requirements of the law have been met, this certificate extends the term of the patent for the period of

2 YEARS with all rights pertaining thereto as provided by 35 USC 156 (b).

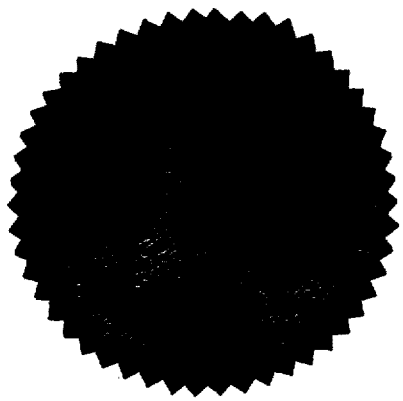

I have caused the seal of the Patent and Trademark Office to be affixed this Twentieth-seventh day of March 1989.

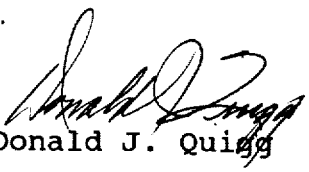
Donald J. Quigg

Assistant Secretary and Commissioner of Patents and Trademarks